(12) United States Patent
Park et al.

(10) Patent No.: US 12,408,870 B2
(45) Date of Patent: Sep. 9, 2025

(54) MASK APPARATUS AND METHOD FOR CONTROLLING THE SAME

(71) Applicant: LG ELECTRONICS INC., Seoul (KR)

(72) Inventors: Sooyong Park, Seoul (KR); Jinmoo Park, Seoul (KR); Seonghun Lee, Seoul (KR); Junchan Kwon, Seoul (KR); Minsoo Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 660 days.

(21) Appl. No.: 17/847,382

(22) Filed: Jun. 23, 2022

(65) Prior Publication Data

US 2023/0015788 A1    Jan. 19, 2023

(30) Foreign Application Priority Data

Jul. 19, 2021  (KR) .................... 10-2021-0094297

(51) Int. Cl.
*H04R 25/00*  (2006.01)
*A61B 5/00*  (2006.01)
*A62B 18/02*  (2006.01)

(52) U.S. Cl.
CPC .......... *A61B 5/6843* (2013.01); *A61B 5/6803* (2013.01); *A61B 5/7264* (2013.01);
(Continued)

(58) Field of Classification Search
CPC ... A61B 5/6843; A61B 5/6803; A61B 5/7264; A61B 5/741; A61B 5/746; A61B 2562/0247; A62B 18/025
(Continued)

(56) References Cited

U.S. PATENT DOCUMENTS 5,307,793 A    5/1994  Sinclair et al.
7,342,502 B2 *  3/2008  Harkins ................. H04B 1/385
                                                          455/90.1
(Continued)

FOREIGN PATENT DOCUMENTS

CN   103127633    6/2013
CN   108939336    12/2018
(Continued)

OTHER PUBLICATIONS

Chinese Office Action dated Feb. 16, 2023 issued in Application No. 202210849481.8.
(Continued)

*Primary Examiner* — William J Deane, Jr.
(74) *Attorney, Agent, or Firm* — KED & ASSOCIATES, LLP

(57) ABSTRACT

Provided is a method for controlling a mask apparatus. The method for controlling the mask apparatus includes measuring a current pressure value with respect to a mask by using a pressure sensor, comparing each of a preset atmospheric pressure maximum estimation and a preset and a preset atmospheric pressure minimum estimation to the current pressure value; updating the atmospheric pressure maximum estimation and the atmospheric pressure minimum estimation according to the comparison result, and controlling a voice output of a speaker based on a difference between the updated atmospheric pressure maximum estimation and the updated atmospheric pressure minimum estimation.

16 Claims, 17 Drawing Sheets

(52) U.S. Cl.
CPC .............. *A61B 5/741* (2013.01); *A61B 5/746* (2013.01); *A62B 18/025* (2013.01); *A61B 2562/0247* (2013.01)

(58) Field of Classification Search
USPC .................................................. 381/301, 300
See application file for complete search history.

(56) References Cited

U.S. PATENT DOCUMENTS

| | | | |
|---|---|---|---|
| 10,827,244 | B1 | 11/2020 | Ward et al. |
| 2007/0283952 | A1* | 12/2007 | Wilbur ..................... A62B 7/04 128/201.19 |
| 2010/0322442 | A1* | 12/2010 | Namm ..................... H04R 1/08 2/173 |
| 2012/0138051 | A1 | 6/2012 | Curran et al. |
| 2015/0165140 | A1 | 6/2015 | Cappelli et al. |
| 2018/0078798 | A1* | 3/2018 | Fabian .................. A62B 18/10 |
| 2021/0029017 | A1* | 1/2021 | Chen ....................... H04L 45/26 |
| 2022/0080228 | A1 | 3/2022 | Webb et al. |

FOREIGN PATENT DOCUMENTS

| | | |
|---|---|---|
| CN | 104540539 | 5/2020 |
| EP | 3446755 | 2/2019 |
| JP | 2002-210031 | 7/2002 |
| JP | 2015-163090 | 9/2015 |
| KR | 10-2012-0051735 | 5/2012 |
| WO | WO 2020/0129017 | 6/2020 |

OTHER PUBLICATIONS

Korean Office Action issued in Application No. 10-2021-0094297 dated Feb. 14, 2025.

* cited by examiner

MASK APPARATUS AND METHOD FOR CONTROLLING THE SAME

CROSS-REFERENCE TO RELATED APPLICATIONS

The present application claims priority under 35 U.S.C. 119 and 35 U.S.C. 365 to Korean Patent Application No. 10-2021-0094297 (filed on Jul. 19, 2021), which is hereby incorporated by reference in its entirety.

BACKGROUND

The present disclosure relates to a mask apparatus and a method for controlling the same.

A mask may be defined as a hygiene product that covers the user's nose and mouth to filter harmful substances including germs and dust contained in the air when the user inhales and minimize spreads of virus or bad breath discharged when the user exhales to nearby people.

Recently, as the virus that is highly spreadable and highly contagious has spread, it is recommended that individuals wear a mask to go out for safety in order to minimize transmission.

Currently, various types and forms of masks are released in the market, and in particular, in order to minimize the harmful substances contained in the air from directly entering the mask wearer's respiratory tract, a lot of masks equipped with a filter module are being sold.

Chinese Patent 103127633, which is the prior art document, (published on Jun. 5, 2013) discloses a multi-functional mask provided with a community system.

The mask disclosed in the prior art document includes a mask body provided with a filter, an amplification module coupled to the mask body, a communication module, a lighting module, and a help calling module.

Specifically, the mask is configured to cover a user's face, and each of modules performing various functions is installed on a front surface of the mask. When a user wears the mask, external air of the mask passes through the filter and is purified and then flows into the mask, and the introduced purified air may be guided to the user's respiratory tract.

In addition, in a state in which the mask is worn, the user may improve community convenience by using at least one of the amplification module, the communication module, the lighting module, or the help call module.

Particularly, when the user has a conversation while wearing the mask, a voice may be amplified by the amplification module and then output through a speaker. Thus, even in a state in which the face is covered by the mask, the voice in a sealed space may be output to the outside of the mask in the amplified state.

However, the multi-functional mask disclosed in the prior art document has the following limitations.

First, since the fan is driven even when the user takes off the mask, there is a limitation in that noise is generated due to the driving of the fan, and power is wasted. That is, since the fan is driven regardless of whether the mask is worn, the noise may be generated, and a battery may be discharged.

Second, since a microphone and a speaker are driven even when the mask is removed, there is a limitation in that fan noise or ambient noise is amplified and output through the speaker.

Specifically, due to the structure of the compact mask, the microphone and the speaker may be disposed adjacent to each other or disposed in the same sealed space. In this case, there is a limitation in that the voice output from the speaker is input to the microphone adjacent to the speaker, resulting in noise due to howling in the speaker.

Third, when the mask is not in use, it is inconvenient to manipulate a separate button to turn off power of the mask. That is, there is a limitation in that it is cumbersome to turn on/off the power of the mask through a manual operation whenever the mask is frequently worn and taken off, and a sanitary state of the mask is impaired due to the increased number of mask touches.

SUMMARY

Embodiments provide a mask apparatus that is capable of accurately determining whether a mask is worn by using an internal pressure of the mask, and a method for controlling the same.

Embodiments also provide a mask apparatus capable of determining whether a mask is worn and controlling a function of a fan or a speaker according to the result of the determination, and a method for controlling the same.

Embodiments also provide a mask apparatus capable of preventing noise caused by a fan noise or a howling phenomenon from occurring in a state in which the mask is taken off, and a method for controlling the same.

Embodiments also provide a mask apparatus capable of improving convenience and hygiene by minimizing a mask touch for function manipulation, and a method for controlling the same.

Embodiments also provide a mask apparatus capable of accurately determining whether a mask is worn regardless of a change in external environment, and a method for controlling the same.

Embodiments also provide a mask apparatus capable of reducing a data processing time taken to determine whether a mask is worn and minimizing a memory capacity, and a method for controlling the same.

In one embodiment, a method for controlling a mask apparatus includes: measuring a current pressure value with respect to a mask by using a pressure sensor; comparing each of a preset atmospheric pressure maximum estimation and a preset and a preset atmospheric pressure minimum estimation to the current pressure value; updating the atmospheric pressure maximum estimation and the atmospheric pressure minimum estimation according to the comparison result; and controlling a voice output of a speaker based on a difference between the updated atmospheric pressure maximum estimation and the updated atmospheric pressure minimum estimation.

That is, in an embodiment, whether the mask is worn may be determined using the internal pressure of the mask and the set atmospheric pressure estimation, and when the mask is worn, the voice output of the speaker may be activated, and when the mask is not worn, the voice output of the speaker may be deactivated.

Therefore, when the mask is taken off, since the speaker is automatically stopped, there is an advantage in that fan noise and noise due to the howling is prevented from occurring.

In addition, since it is determined whether the mask is worn by using the atmospheric pressure estimation based on the internal pressure of the mask, there is an advantage in that whether the mask is worn is accurately determined regardless of a change in external environment.

The controlling of the voice output of the speaker based on the difference between the updated atmospheric pressure maximum estimation and the updated atmospheric pressure minimum estimation may include: calculating a difference value between the updated atmospheric pressure maximum estimation and the updated atmospheric pressure minimum estimation; comparing the difference value to a reference pressure value; and controlling the voice output of the speaker according to the comparison result of the difference value and the reference pressure value.

When the measured current pressure value is less than the reference pressure value, a voice output function of the speaker may be deactivated, or a voice may be muted.

When the measured current pressure value is greater than the reference pressure value, a voice output function of the speaker may be activated, or a mute state may be released.

Therefore, since the operation of the speaker is automatically controlled without a separate function button operation, the mask touch may be reduced to improve convenience and the sanitary condition of the mask.

The method may further include controlling an operation of a fan module based on a difference between the updated atmospheric pressure maximum estimation and the updated atmospheric pressure minimum estimation.

That is, in an embodiment, whether the mask is worn may be determined using the internal pressure of the mask and the set atmospheric pressure estimation, and when the mask is worn, the fan module may be driven, and when the mask is not worn, the operation of the fan module may be stopped.

Therefore, when the mask is taken off, the driving of the fan may be automatically stopped, and thus, fan noise may be prevented, and power consumption by driving the fan may be prevented.

The atmospheric pressure maximum estimation and the atmospheric pressure minimum estimation may be pressure values defined between a maximum pressure value and a minimum pressure value among the pressure values measured by the pressure sensor.

The updating of the atmospheric pressure maximum estimation and the atmospheric pressure minimum estimation according to the comparison result may include; when the preset atmospheric pressure maximum estimation is less than the current pressure value; updating the preset atmospheric pressure maximum estimation to the current pressure value; and updating the preset atmospheric pressure minimum estimation by reflecting a weight.

When the preset atmospheric pressure maximum estimation exceeds the current pressure value, the preset atmospheric pressure minimum estimation and the current pressure value may be compared to each other, and when the preset atmospheric pressure minimum estimation is equal to or greater than the current pressure value, the preset atmospheric pressure minimum estimation may be updated to the current pressure value to update the preset atmospheric pressure maximum estimation by reflecting a weight.

When the preset atmospheric pressure maximum estimation exceeds the current pressure value, and the preset atmospheric pressure maximum estimation is less than the current pressure value, each of the preset atmospheric pressure maximum estimation and the preset atmospheric pressure maximum estimation may be updated by reflecting the weight.

In another embodiment, a method for controlling a mask apparatus includes: measuring a pressure value of a mask for a predetermined time by using a pressure sensor; calculating a difference value between a maximum pressure value and a minimum pressure value among pressure values measured for the predetermined time; and controlling a voice output of a speaker based on the difference value between the maximum pressure value and the minimum pressure value.

That is, according to another embodiment, whether the mask is worn may be determined using only an internal pressure of the mask, and when the mask is worn, a voice output of a speaker may be activated, and when the mask is not worn, the voice output of the speaker may be deactivated. Therefore, when the mask is taken off, since the speaker is automatically stopped, there is an advantage in that fan noise and noise due to the howling is prevented from occurring.

The controlling of the voice output of the speaker based on the difference value between the maximum pressure value and the minimum pressure value may include: comparing the difference value to a reference pressure value; and controlling the voice output of the speaker according to the comparison result of the difference value and the reference pressure value.

When the difference value is less than the reference pressure value, the voice output function of the speaker may be deactivated, or a sound may be muted.

When the difference value is greater than the reference pressure value, the voice output function of the speaker may be activated, or the mute state may be released.

Therefore, since the operation of the speaker is automatically controlled without a separate function button operation, the mask touch may be reduced to improve convenience and the sanitary condition of the mask.

In further another embodiment, a mask apparatus includes: a mask body in which a microphone and a speaker are installed; a face guard coupled to the mask body so as to be in close contact with a user's face and having a breathing space therein; a pressure sensor installed in the mask body to measure a pressure of the breathing space; and a controller configured to: compare a preset atmospheric pressure maximum estimation to an atmospheric pressure minimum estimation to a current pressure value measured by the pressure sensor; update the atmospheric pressure maximum estimation and the atmospheric pressure minimum estimation according to the comparison result; and control a voice output of the speaker based on a difference between the updated atmospheric pressure maximum estimation and the updated atmospheric pressure minimum estimation.

The details of one or more embodiments are set forth in the accompanying drawings and the description below. Other features will be apparent from the description and drawings, and from the claims.

DETAILED DESCRIPTION OF THE EMBODIMENTS

Reference will now be made in detail to the embodiments of the present disclosure, examples of which are illustrated in the accompanying drawings.

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense.

Also, in the description of embodiments, terms such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, the former may be directly "connected," "coupled," and "joined" to the latter or "connected", "coupled", and "joined" to the latter via another component.

Figure 1:
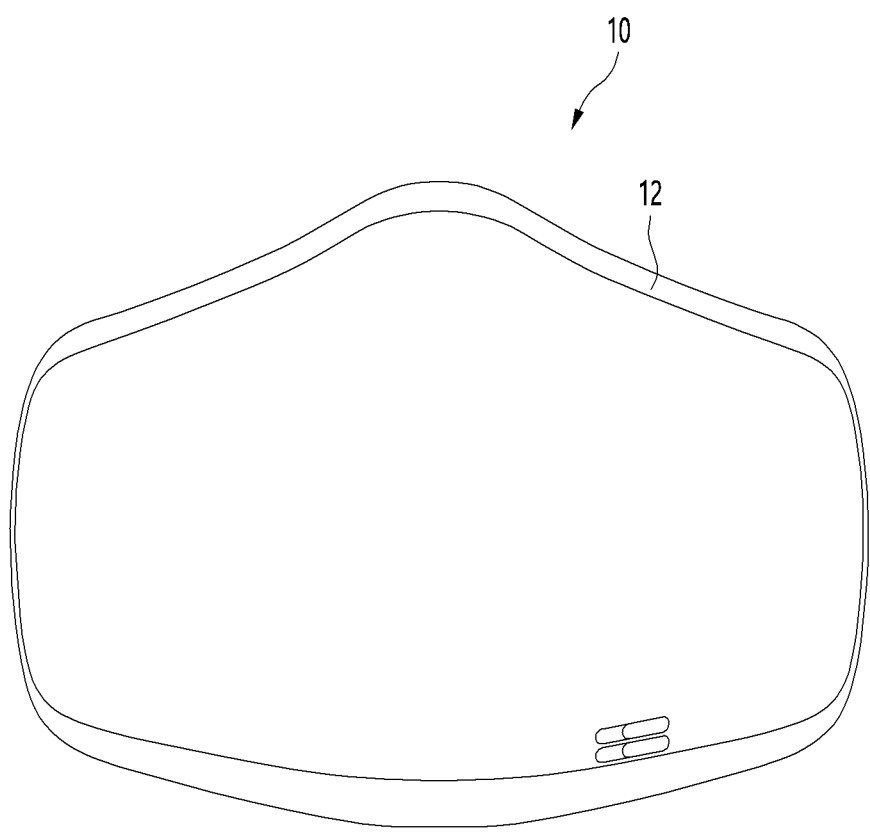
FIG. 1 is a front view of a mask apparatus according to an embodiment.
Figure 2:
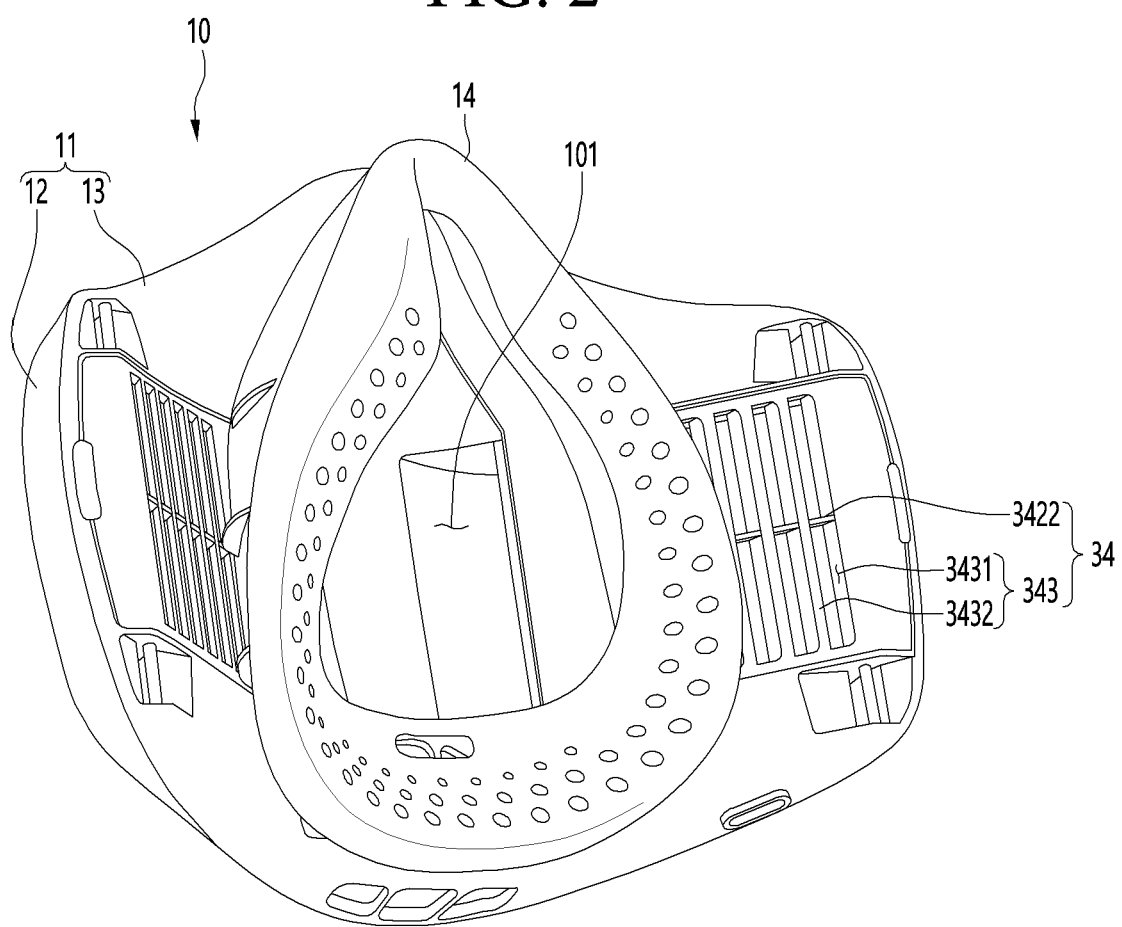
FIG. 2 is a rear perspective view of the mask apparatus.
Figure 3:
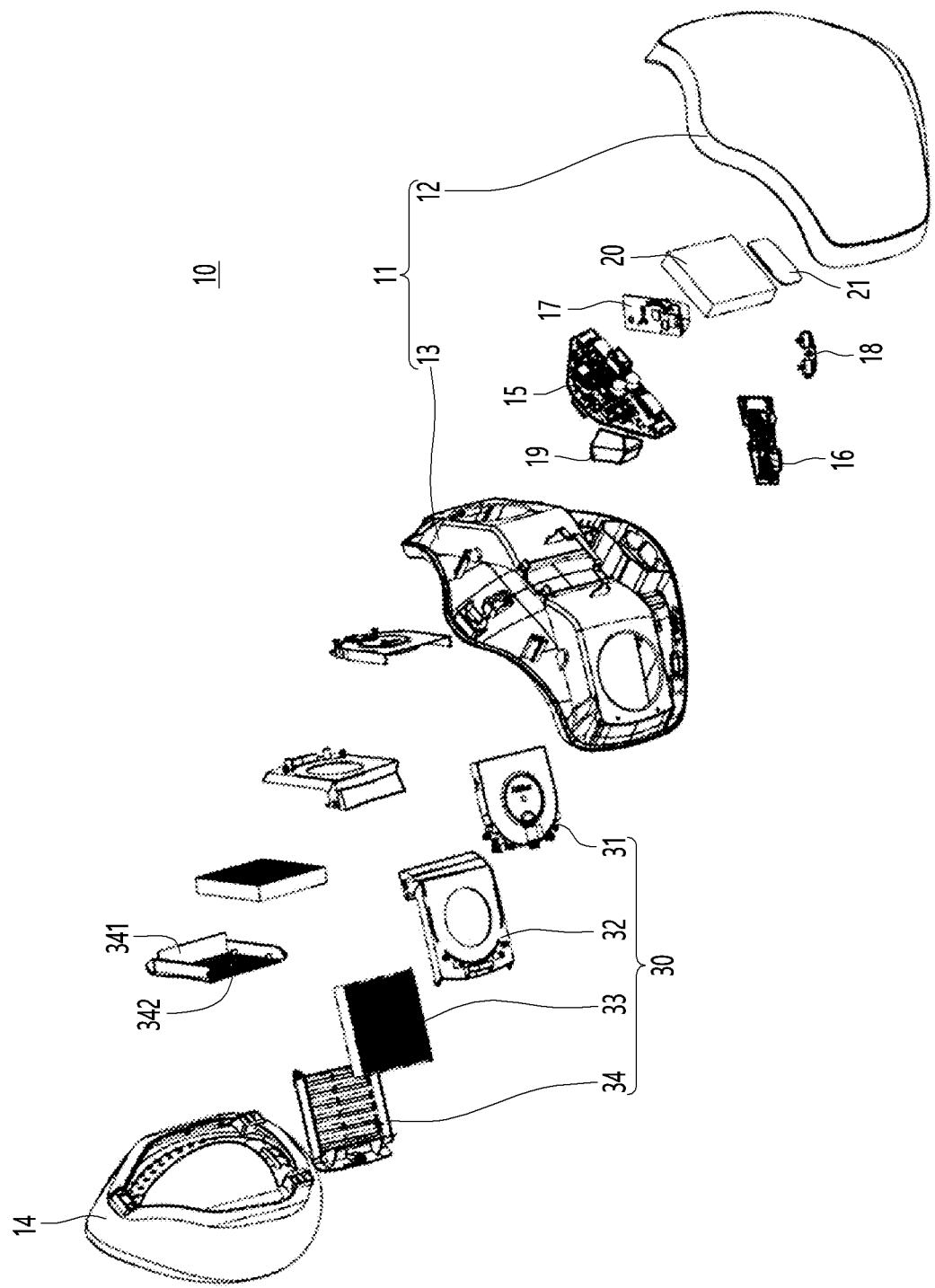
FIG. 3 is an exploded perspective view of the mask apparatus.
Figure 4:
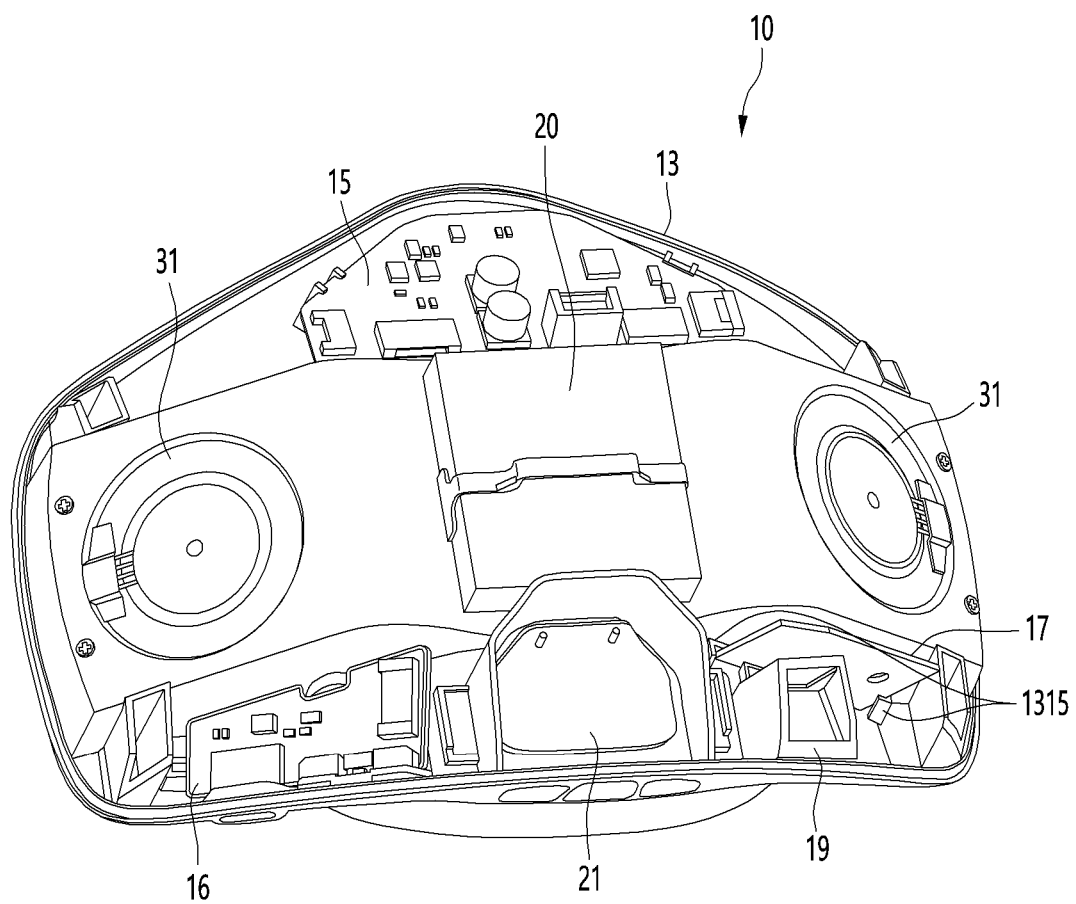
FIG. 4 is a front perspective view of the mask apparatus from which a front body is separated.

FIG. 1 is a front view of a mask apparatus according to an embodiment, FIG. 2 is a rear perspective view of the mask apparatus, FIG. 3 is an exploded perspective view of the mask apparatus, and FIG. 4 is a front perspective view of the mask apparatus from which a front body is separated.

Referring to FIGS. 1 to 4, a mask apparatus 10 according to an embodiment includes a mask body 11, a face guard 14 that is fixedly or detachably coupled to a rear surface of the mask body 11, and an air cleaning module 30 mounted inside the mask body 11.

In detail, the mask body 11 includes a front body 12 defining an outer appearance of a front surface and a rear body 13 coupled to a rear surface of the front body 12 to define an outer appearance of a rear surface. The front surface of the front body 12 defines a front surface of the mask apparatus 10, and the rear surface of the rear body 13 faces a face of a user (or a wearer).

In addition, the face guard 14 may be coupled to the rear surface of the rear body 13 so as to be in close contact with the user's face and may be made of a silicone or rubber material having elasticity. A breathing space is defined inside the face guard 14, and when the user wears the mask apparatus 10, a user's nose and mouth are accommodated in the breathing space. Thus, external air purified while passing through the air cleaning module 30 is guided to the breathing space and inhales by the user, and air generated when the user exhales is also discharged into the breathing space.

A predetermined space is defined between the front body 12 and the rear body 13, and as illustrated in FIG. 4, various electrical components are mounted on the front surface of the rear body 13. In addition, the various electrical components are shielded by the front body 12 so as not to be exposed to the outside.

In addition, the air cleaning module 30 includes a fan module 31 placed in an accommodation portion 133 (see FIG. 6) provided in the rear body 13 and a filter 33 placed behind the fan module 31. The fan module 31 includes a centrifugal fan that suctions air in an axial direction to discharge the air in a radial direction.

The air cleaning module 30 further includes a filter housing 34 disposed behind the filter 33, and a suction hole through which external air is suctioned is defined in the filter housing 34. The filter housing 34 may be rotatably coupled to the rear body 13, and the suction hole may be provided in the form of a suction grill 343 as illustrated in the drawings.

In detail, the filter housing 34 includes a filter frame 341 surrounding three side surfaces of the filter 33, and a filter cover 342 disposed on a rear surface of the filter frame 341. The filter cover 342 includes a suction grill 343.

The suction grill 343 may be understood as a structure including a plurality of suction slits 3431 and a plurality of partition ribs 3432 disposed between the adjacent suction slits 343. The suction grill 343 may be understood as a structure in which one large suction hole is divided into a plurality of narrow and long suction slits 3431 by the plurality of partition ribs 3432. In addition, the plurality of narrow and long suction slits 3431 may be divided into an upper slit and a lower slit by a reinforcing rib 3422. Hereinafter, the suction hole defined in the rear surface of the mask apparatus 10 to suction the external air is defined as including various types of holes including the suction grill 343, and the suction hole of the mask body 11 and the suction grill 343 should be interpreted as the same meaning.

In addition, a discharge hole 101 is defined at a point spaced apart from the suction hole in a central direction of the rear body 13. The external air suctioned through the suction hole or the suction grill 343 by an operation of the fan module 31 sequentially passes through the filter 33 and the fan module 31 and then is discharged into the breathing space through the discharge hole 101.

The suction hole, i.e., the suction grill 343 is disposed outside the face guard 14, and the discharge hole 101 is disposed inside the face guard 14. That is, the suction grill 343 is disposed outside the breathing space, and the discharge hole 101 is defined inside the breathing space, and thus, the suctioned external air and the air exhaled by the user are not mixed with each other.

The air cleaning module 30 further includes a flow guide 32 disposed behind the fan module 31.

In addition, the mask apparatus 10 further includes at least one of a main control module 15, a power module 16, an indicator module 18, a wireless communication module 17, a speaker module 19, and a battery 20, or an exhaust valve 21.

In detail, the main control module 15 is a module for controlling operations of the fan module 31, the speaker module 19, and a pressure sensor and a microphone, which will be described later. The main control module 15 may be disposed on an upper portion of a center of the front surface of the rear body 13.

The power module 16 is a control module for supplying power to the electric components mounted on the mask apparatus 10. The power module 16 may be disposed at a right lower end of the front surface of the rear body 13.

A cable connector, into which a terminal of a cable for power supply and data transmission is inserted, and an LED module used to inform an operation state of the mask apparatus 10 may be mounted on the power module 16. Then, light irradiated from the LED module is diffused and guided through the indicator module 18 and then is emitted to the outside of the mask apparatus 10.

The wireless communication module 17 may be any one of various types of short-range wireless communication modules including Bluetooth. The wireless communication module 17 may be disposed on a left lower end of the front surface of the rear body 13. The wireless communication module 17 may be mounted on the front surface of the rear body 13 in a direction crossing the rear body 13, for example, horizontally. The wireless communication module 17 may be mounted on the front surface of the rear body 13 in a horizontal state by a pair of substrate insertion ribs 1315 protruding from the front surface of the rear body 13. Both side ends of the wireless communication module 17 are supported by the pair of substrate insertion ribs 1315.

The speaker module 19 may be disposed on the left lower end of the front surface of the rear body 13 corresponding to a lower side of the wireless communication module 17.

The battery 20 may be disposed at a center of the front surface of the rear body 13, and the exhaust valve 21 may be disposed to shield an exhaust port provided below the center of the front surface of the rear body 13. That is, when the user exhales, the exhaust valve 21 may open the exhaust port, and when the user inhales, the exhaust valve 21 may block the exhaust port. The exhaust valve 21 may be bent and provided in the form of a flat flap.

Here, it should be noted that the front, rear, left, and right sides of the mask body 11 are defined based on a state in which the user wears the mask apparatus 10.

Figure 5:
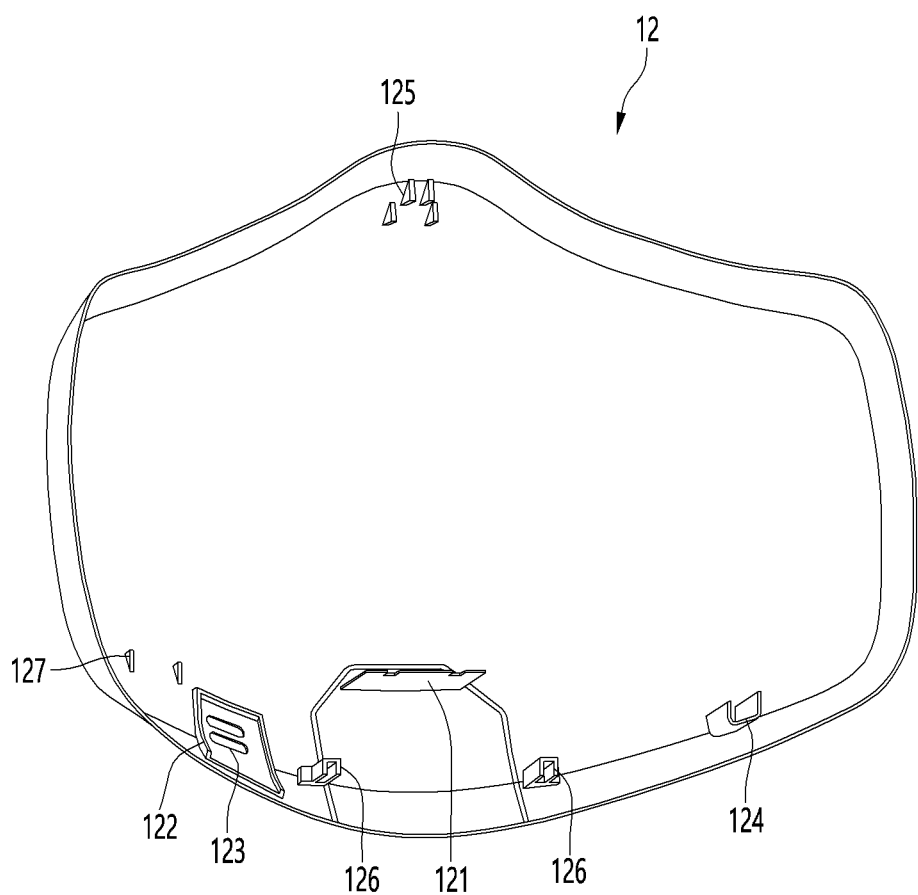
FIG. 5 is a rear perspective view of a front body constituting the mask apparatus according to an embodiment.

FIG. 5 is a rear perspective view of the front body constituting the mask apparatus according to an embodiment.

Referring to FIG. 5, the front body 12 constituting the mask apparatus 10 according to the embodiment defines an outer appearance of the front surface of the mask apparatus 10.

When the front surface of the front body 12 is provided as a single body without a separate component mounted thereon, it has the advantage of being clean in outer appearance. When the suction hole is defined at each of the left and right sides of the front body 12, if the suction hole is placed to face an upper side after taking off the mask apparatus 10, there is disadvantage in that possibility, in which foreign substances are introduced into the mask apparatus 10 through the suction hole, is high.

In addition, when a separate cover is installed to shield the suction hole, thereby minimizing the inflow of the foreign substances, a gap needs to be defined between an edge of the cover and the front surface of the front body 12 so that external air is introduced. That is, there is a restriction that the separate cover has to be coupled to the front surface of the front body 12 in the form that protrudes from the front surface of the front body 12.

As a result, there is a high possibility that the separate cover is damaged by external force or be separated from the front body 12 by being caught by a surrounding obstacle. For this reason, it is advantageous in appearance to design the front body 12 so that the suction hole for inhaling the external air is not defined as much as possible to prevent a separate component from protruding due to additional mounting of the separate component on the front surface of the front body 12, and also it is advantageous for securing durability.

In consideration of this aspect, the suction hole for suctioning the external air is not defined in the front surface of the front body 12 according to the embodiment of the present invention, and also, additional components including the cover are not mounted at all, and thus, the front surface is designed so that a smooth and continuous single surface is provided. However, a speaker hole 123 is defined in a side of the lower portion so that user's voice is output to the outside.

A plurality of protrusion structures are disposed on the rear surface of the front body 12.

In detail, one or plurality of substrate fixing ribs 125 protrude from an upper end of the center of the rear surface of the front body 12. The one or plurality of substrate fixing ribs 125 may press a front surface of the main control module 15 mounted on the rear body 13 when an edge of the front body 12 is coupled to an edge of the front surface of the rear body 13 to prevent the main control module 15 from being oscillated.

A valve support rib 121 horizontally protrudes from the rear surface of the front body 12. The valve support rib 121 is disposed at a point at which an upper end of the exhaust valve 21 is disposed when the front body 12 is coupled to the rear body 13, to press an upper end of a front surface of the exhaust valve 21. For example, the valve support rib 121 may have a predetermined width and extend backward by a predetermined length at a point spaced a predetermined distance downward from the center of the rear surface of the front body 12.

In addition, a pair of magnet pressing ribs 126 may protrude from the rear surface of the front body 12. In detail, the face guard 14 is mounted on the rear surface of the rear body 13, a magnet is mounted on a front surface of the face guard 14, and a magnet that is attractive to the magnet is mounted on the front surface of the rear body 13. As a result, the face guard 14 is detachably mounted on the rear surface of the rear body 13 by the magnetic force of the magnet.

At this time, a pair of lower magnet mounting portions 135 (see FIG. 6) for mounting the magnet are disposed on the front surface of the rear body 13. In addition, the pair of magnet pressing ribs 126 function to press the pair of magnets mounted on the pair of lower magnet mounting portions 135, respectively.

In addition, a substrate pressing rib 127 that is in contact with a front end of a substrate constituting the wireless communication module 17 protrudes from the rear surface of the front body 12. In detail, when the front body 12 and the rear body 13 are coupled to each other, the substrate pressing rib 127 presses the front end of the substrate constituting the wireless communication module 17 to prevent the wireless communication module 17 from being oscillated or being separated from the substrate insertion rib 1315.

In addition, a support rib 122 supporting and surrounding an edge of the front end of the speaker module 19 is disposed on the rear surface of the front body corresponding to an edge of the speaker hole 123. The support rib 122 may be surrounded in a shape corresponding to a shape of the front surface of the speaker module 19.

In addition, a substrate fixing rib 124 for pressing a front surface of the power module 16 protrudes from the rear surface of the front body 12. The substrate fixing rib 124 presses a front surface of the substrate constituting the power module 16 to prevent the power module 16 from oscillated or being separated from the rear body 13.

Figure 6:
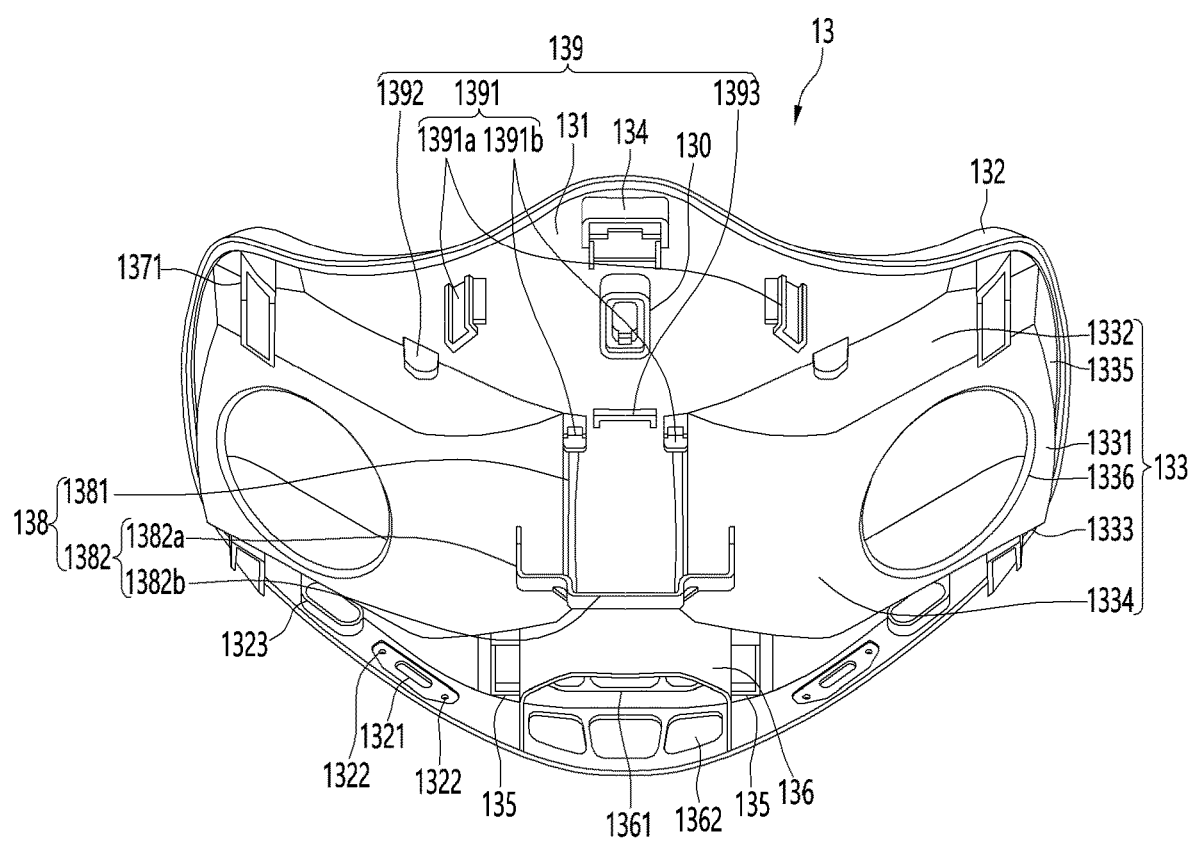
FIG. 6 is a front perspective view of a rear body constituting the mask apparatus according to an embodiment.
Figure 7:
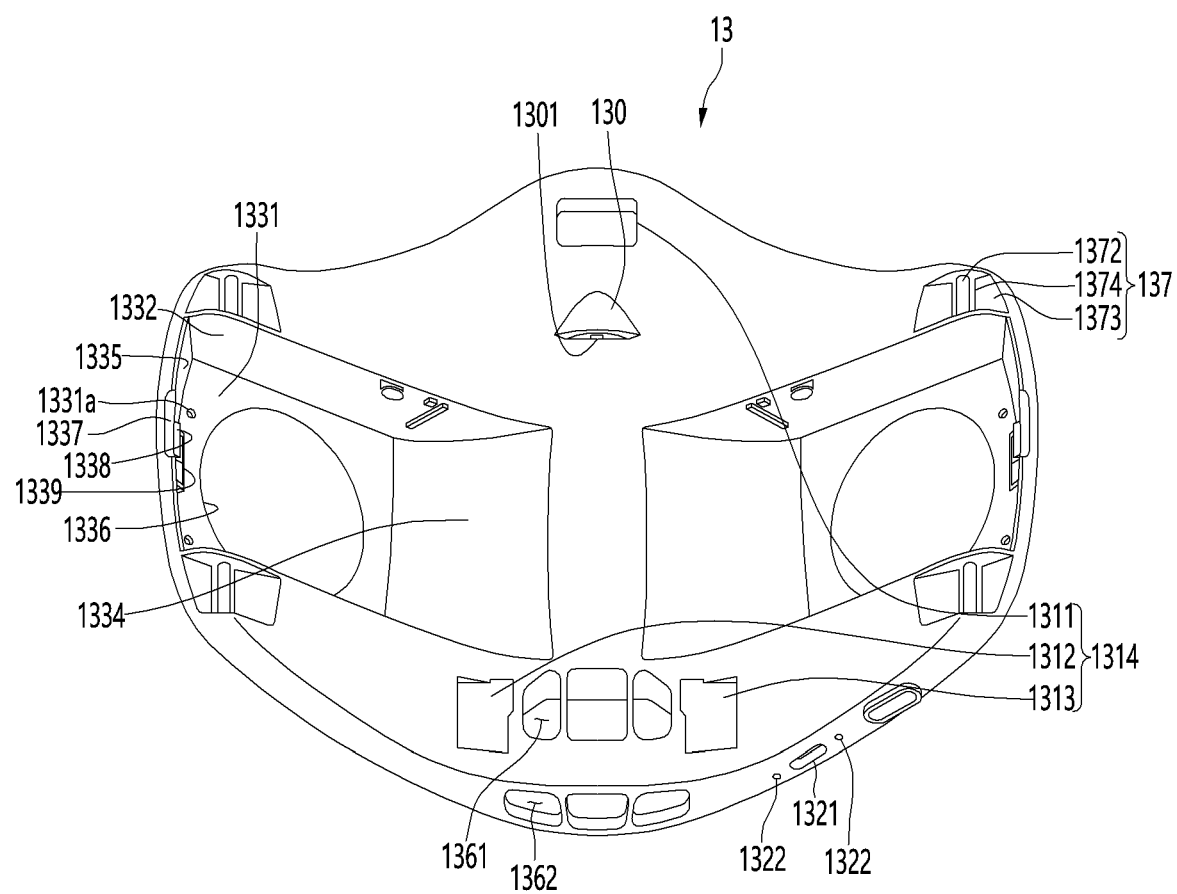
FIG. 7 is a rear perspective view of the rear body.

FIG. 6 is a front perspective view of the rear body constituting the mask apparatus according to an embodiment, and FIG. 7 is a rear perspective view of the rear body.

Referring to FIGS. 6 and 7, the rear body 13 constituting the mask apparatus 10 according to the embodiment includes a face cover portion 131 that covers a user's face and a fusion portion 132 bent forward from an edge of the face cover portion 131.

In detail, the fusion portion 132 is continuously disposed along an edge of a top surface, edges of both surfaces, and an edge of a bottom surface of the face cover portion 131. In addition, a width of the fusion portion 132 in a front and rear direction, which is bent along an edge of a bottom surface of the face cover portion 13 to extend forward is the largest.

In the fusion portion 132, a portion disposed on the edge of the bottom surface of the face cover portion 131 may be specifically defined as an extension protrusion. The extension protrusion has a convexly rounded shape in such a manner that a width in the front and rear direction gradually increases from both side ends of the rear body 13 toward the center.

A bottom surface exhaust hole 1362 is disposed at a center of the fusion portion 132 defined as the extension protrusion, and a button hole 1321 is defined at a point spaced apart from the bottom exhaust port 1362 toward a side end of the rear body 13. A power button is inserted into the button hole 1321. An indication hole 1322 is defined at a point spaced apart from each of left and right edges of the button hole 1321.

Light irradiated from a light emitting unit mounted on the power module 16 is emitted to the outside through the pair of indication holes 1322. The light emitting unit includes an LED module.

When the light is emitted to the outside through any one of the pair of indication holes 1322, it may mean that the power of the mask apparatus 10 is turned on. In addition, a remaining amount of battery 20 may be predicted according to a color of the light emitted through the other one of the pair of indication holes 1322.

A terminal insertion hole 1323 is defined at a point further spaced apart from the button hole 1321 toward the side end of the rear body 13. A universal serial bus (USB) cable may be inserted into a terminal connector provided in the power module 16 through the terminal insertion hole 1323. The battery 20 is charged through the USB cable, and a version or function of the mask apparatus 10 may be updated or upgraded by data transmitted through the USB cable.

A accommodation portion 133 for accommodating the air cleaning module 30 is provided in the rear body 13. The accommodation portion 133 is provided at each of left and right sides from the center of the rear body 13, and the pair of accommodation portions 133 are symmetrical with respect to a vertical line passing through the center of the rear body 13.

The accommodation portion 133 protrudes forward from the front surface of the face cover portion 131 to define a space in which the air cleaning module 30 is accommodated. The accommodation portion 133 includes a seating surface 1331 on which the air cleaning module 30, specifically, the fan module 31 is seated, a coupling surface 1335 connecting an outer edge of the seating surface 1331 at a side end of the face cover portion 131, and an air guide surface 1334 connecting the front surface of the face cover portion 131 at an inner edge of the seating surface 1331.

In addition, the accommodation portion 133 further include a top surface 1332 connecting upper ends of the seating surface, the air guide surface 1334, and the coupling surface 1335 to the front surface of the face cover portion 131. In addition, the accommodation portion 133 further include a bottom surface 1332 connecting lower ends of the seating surface, the air guide surface 1334, and the coupling surface 1335 to the front surface of the face cover portion 131.

One or more coupling units, for example, coupling hooks, are disposed on the coupling surface 1335.

A fan mounting hole 1336 may be defined in the seating surface 1331, and the top surface 1332 and the bottom surface 1334 may extend horizontally and extend parallel to each other.

The coupling surface 1335 may be convexly rounded toward the outside of the rear body 13 and be inclined toward the center of the rear body 13 from the face cover portion 131 to the seating surface 1331.

The air guide surface 1334 may be designed to extend convexly and roundly from the seating surface 1331 toward the face cover portion 131 so that air suctioned by the fan module 31 is smoothly guided toward the discharge hole 101 along the air guide surface 1334.

As another example, the air guide surface 1334 is constituted by a round portion that is rounded with a predetermined curvature at the inner edge of the seating surface 1331 and an inclined portion connecting the face cover portion 131 flatly and obliquely at an end of the round portion.

The accommodation portion 133 includes a left accommodation portion disposed at the left side from the center of the rear body 13 and a right accommodation portion disposed at the right side from the center of the rear body 13. The left accommodation portion and the right accommodation portion are spaced a predetermined distance from the center of the rear body 13, and the battery 20 is mounted in a space between the left accommodation portion and the right accommodation portion.

A battery mounting portion 138 may be disposed on the front surface of the rear body 13. In detail, the battery mounting portion 138 includes a pair of battery seating ribs 1381 and a battery support rib 1382.

The pair of battery seating ribs 1381 protrude forward from the front surface of the face cover portion 131 or an edge of the air guide surface 1334 to extend in parallel in the vertical direction. The pair of battery seating ribs 1381 supports a rear surface of the battery 20.

One end of the battery support rib 1382 extends from either one of the left air guide surface 1334 and the right air guide surface 1334, and the other end is connected to the other side of the left air guide surface 1334 and the right air guide surface 1334.

The battery support rib 1382 has an n-shape to support the front and both surfaces of the battery 20. Thus, a phenomenon in which the battery 20 is separated from the rear body 13 may be prevented by the battery support rib 1382.

In addition, a central portion of the battery support rib 1382 protrudes forward so that a battery having a different size is selectively mounted.

In detail, the battery support rib 1382 includes a pair of extension portions extending forward from the pair of air guide surfaces 1334 and a connection portion extending in a horizontal direction to connect the pair of extension portions to each other.

In addition, a portion of the connection portion is bent to extend forward, so that the battery support rib 1382 is described as being constituted by a first battery support 1382*a* and a second battery support 1382*b*. In detail, the first battery support 1382*a* may be used to support a relatively wide and thin battery, and the second battery support 1382*b* may be used to support a relatively narrow and thick battery.

The second battery support 1382*b* may be described as being provided by bending a portion of the connection portion constituting the first battery support 1382*a* forward a plurality of times. Alternatively, it may be described that the relatively small n-shaped second battery support 1382*b* protrudes from a front surface of the relatively large n-shaped first battery support 1382*a*.

An exhaust passage guide 136 protrudes forward from the front surface of the face cover portion 131 corresponding to a lower side of the battery mounting portion 138. In detail, the exhaust passage guide 136 is disposed below the battery mounting portion 138, and a lower end of the battery 20 mounted on the battery mounting portion 138 is supported by a top surface of the exhaust passage guide 136. As a result, it is possible to prevent the battery 20 from being pulled downward due to gravity while being inserted into the battery mounting portion 138.

The exhaust passage guide 136 may have a substantially tunnel-shaped longitudinal cross-section, and a front exhaust port 1361 may be disposed on the face cover portion 131 corresponding to the inside of the exhaust passage guide 136.

At least one of the front exhaust port 1361 or the bottom exhaust port 1362 may be provided in the form of an exhaust grill divided into a plurality of small exhaust ports by a plurality of grills or partition ribs. In addition, the front exhaust port 1361 is selectively opened and closed by the exhaust valve 21.

An upper magnet mounting portion 134 is disposed at the upper end of the center of the front surface of the face cover portion 131, and a pair of lower magnet mounting portions 135 are disposed on a lower end of the front surface of the face cover portion 131.

In detail, the lower magnet mounting portion 135 is disposed on each of a left edge and a right edge of the exhaust passage guide 136. The magnet mounted on the lower magnet mounting portion 135 is pressed by the pair of magnet pressing ribs 126 (see FIG. 5) protruding from the rear surface of the front body 12.

A strap connection portion 137 is disposed at each of the left end and the right end of the rear body 13. In detail, the strap connection portion 137 is a portion to which an end of a strap or band that is caught on the user's ear or wraps around the back of the user's head is connected. The strap connection portion 137 is disposed at each of upper and lower portions of the left and right ends of the rear body 13.

Both ends of any one of the pair of straps may be respectively connected to the strap connection portions 137 provided at the upper left and lower ends, and both ends of the other one may be respectively connected to the strap connection portions 137 provided at the upper right and lower ends. Then, the pair of straps may be hung on both user's ears, respectively.

As another method, both ends of any one of the pair of straps may be respectively connected to the strap connection portions 137 provided at the upper left and right ends, and both ends of the other one may be respectively connected to the strap connection portions 137 provided at the lower left and right ends. Then, the pair of straps may be wrapped around the user's back of the head.

Each of the four strap connection portions 137 includes a strap groove 1373 that is recessed from the front surface of the rear body 13 to extend in the horizontal direction (width direction of the rear body), a strap hole 1374 defined in any point of the strap groove 1373, a strap bar 1372 connecting top and bottom surfaces of the strap groove 1373 to each other, and a tubular waterproof rib 1371 extending from the rear surface of the rear body 13 corresponding to an edge of the strap hole 1374.

A main control module mounting portion 139 is disposed on the front surface of the rear body 13.

In detail, the main control module mounting portion 139 includes a substrate fixing hook 1391 protruding forward from the front surface of the face cover portion 131 and a substrate seating rib 1393 and substrate support rib 1392, which support a rear surface of the main control module 13.

In detail, the substrate fixing hook 1391 may include a pair of first substrate fixing hooks 1391*a* disposed above the accommodation portion 133 and a pair of second fixing hooks 1391*b* disposed between the pair of accommodation portions 133 facing each other.

The pair of first substrate fixing hooks 1391*a* may be disposed at a point spaced upward from a top surface of the left accommodation portion and at a point spaced upward from a top surface of the right accommodation portion. The pair of first substrate fixing hooks 1391*a* function to fix left and right ends of the main control module 15.

In addition, the pair of second substrate fixing hooks 1391*b* may be respectively disposed at points corresponding to inner upper ends of the pair of accommodation portions 133. In detail, any one of the pair of second substrate fixing hooks 1391*b* may be disposed at a point at which an upper edge of the right accommodation portion meets the front surface of the face cover portion 131. In addition, the other of the pair of second substrate fixing hooks 1391*b* may be disposed at a point at which an upper edge of the left accommodation portion meets the front surface of the face cover portion 131.

The pair of second substrate fixing hooks 1391*b* function to fix a lower end of the control substrate constituting the main control module 15.

In addition, the substrate seating rib 1392 may protrude from the front surface of the face cover portion 131 corresponding between the pair of second substrate fixing hooks 1391*b* to support a rear surface of the lower end of the control substrate constituting the main control module 15.

In addition, a rear surface of the upper end of the main control module 15 may be supported by a front end of the upper magnet mounting portion 134. The main control module 15 is disposed to be spaced apart from the face cover portion 131 by the upper magnet mounting portion 134 and the substrate seating rib 1393, and thus, there is an effect that the main control module 15 is stably coupled to the rear body without oscillated by the substrate fixing hook 1391.

A pressure sensor mounting portion (or breathing sensor mounting portion) 130 may be disposed at a center of the upper portion of the front surface of the face cover portion 131. A pressure sensor (to be described later) mounted on the pressure sensor mounting portion 130 senses a pressure in the breathing space defined inside the face guard 14. That is, it may be determined whether the user is currently inhaling or exhaling according to a change in pressure inside the breathing space. The pressure sensor may be defined as a breathing sensor, and although the terms are different, it should be understood as a sensor performing the same function.

The pressure sensor mounting portion 130 is provided on the front surface of the rear body 13, and when the main control module 15 is mounted on the main control module mounting portion 139, the pressure sensor mounting portion 130 is disposed at a point at which the pressure sensor (or breathing sensor) mounted on the rear surface of the main control module 15 is disposed. Thus, when the main control module 15 is mounted to the main control module mounting portion 139, the pressure sensor is accommodated in the pressure sensor mounting portion 130. In addition, a front end of the pressure sensor mounting portion 130 is in close contact with the rear surface of the control substrate of the main control module 15.

In addition, a portion defining a bottom of the pressure sensor mounting portion 130 protrudes to a rear side of the rear body 13, and a through-hole 1301 is defined in a bottom surface of the portion protruding backward. The breathing space defined by the rear surface of the rear body 13 and the face guard 14 and an inner space of the pressure sensor mounting portion 130 communicate with each other through the through-hole 1301. As a result, a portion of air generated when the user exhales flows into the inner space of the pressure sensor mounting portion 130 through the through-hole 1301. In addition, the pressure sensor accommodated in the pressure sensor mounting portion 130 senses a pressure inside the pressure sensor mounting portion 130. Then, the sensed pressure value is transmitted to a microcomputer (to be described later) of the main control module 15 so that a user's breathing state is determined.

A magnet mounting groove 1314 is defined each of the rear surface of the rear body 13 corresponding to a direct rear surface of the upper magnet mounting portion 134 and the rear surface of the rear body 13 corresponding to a direct rear surface of the pair of lower magnet mounting portions 135.

The magnet mounting groove 1314 includes a first magnet mounting groove 1311 defined in a direct rear surface of the upper magnet mounting portion 134 and a second magnet mounting groove 1312 and a third magnet mounting groove 1313, which are defined in a direct rear surface of the lower magnet mounting portion 134.

Three magnets mounted on the face guard 14 are attached to the first to third magnet mounting grooves 1311 to 1313 by magnetic force, respectively. In addition, when the user pulls the face guard 14 with force greater than the magnetic force, the face guard 14 is easily separated from the rear body 13.

As described above, the fan mounting hole 1336 may be defined in the seating surface 1331 constituting the accommodation portion 133. In addition, one or plurality of flow guide coupling holes 1331a are defined at a point spaced apart from the fan mounting hole 1336 toward the outer edge of the seating surface 1331. The flow guide 32 is fixed to the accommodation portion 133 by a coupling member passing through the flow guide coupling hole 1331a.

In addition, a flow guide hook 1339 and a filter hook 1338 are disposed to be spaced apart from each other in the front and rear direction on the coupling surface 1335 constituting the accommodation portion 133. The flow guide hook 1339 is disposed closer to the seating surface 1331 than the filter hook 1338.

In addition, a gripping groove 1337 is defined at a side end of the rear surface of the rear body 13 corresponding to a rear side of the filter hook 1338. In detail, it may be described that the gripping groove 1337 is defined at a point at which the fusion portion 132 and the coupling surface 1335 meet each other.

Figure 8:
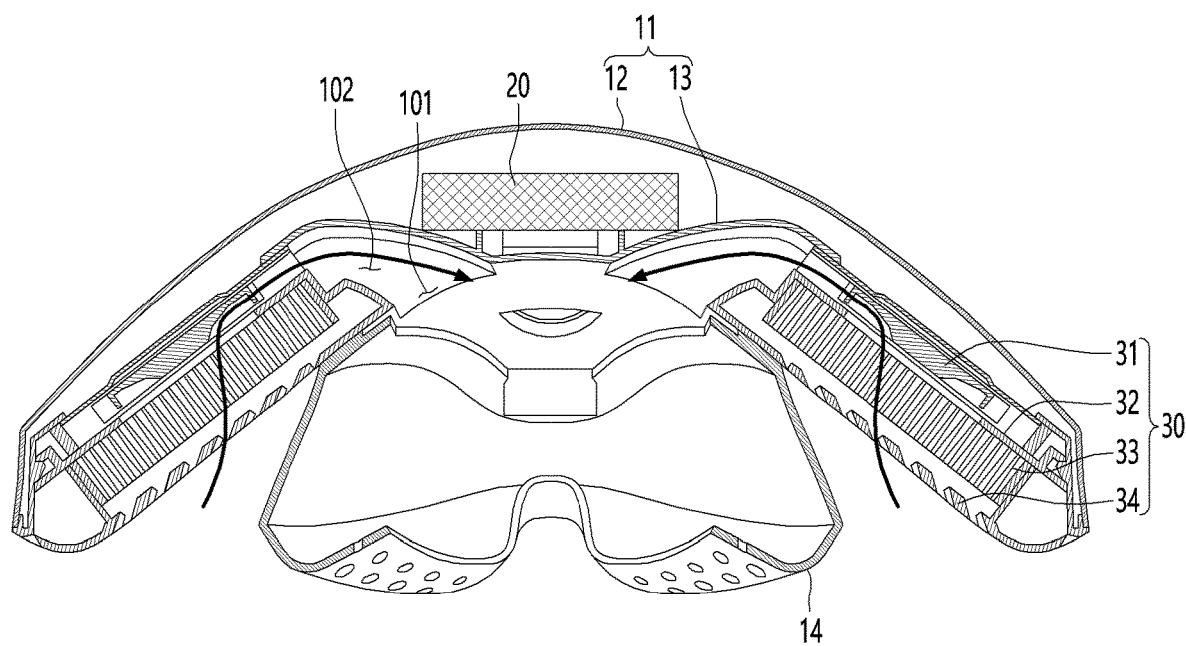
FIG. 8 is a transverse cross-sectional view of the mask apparatus according to an embodiment.
Figure 9:
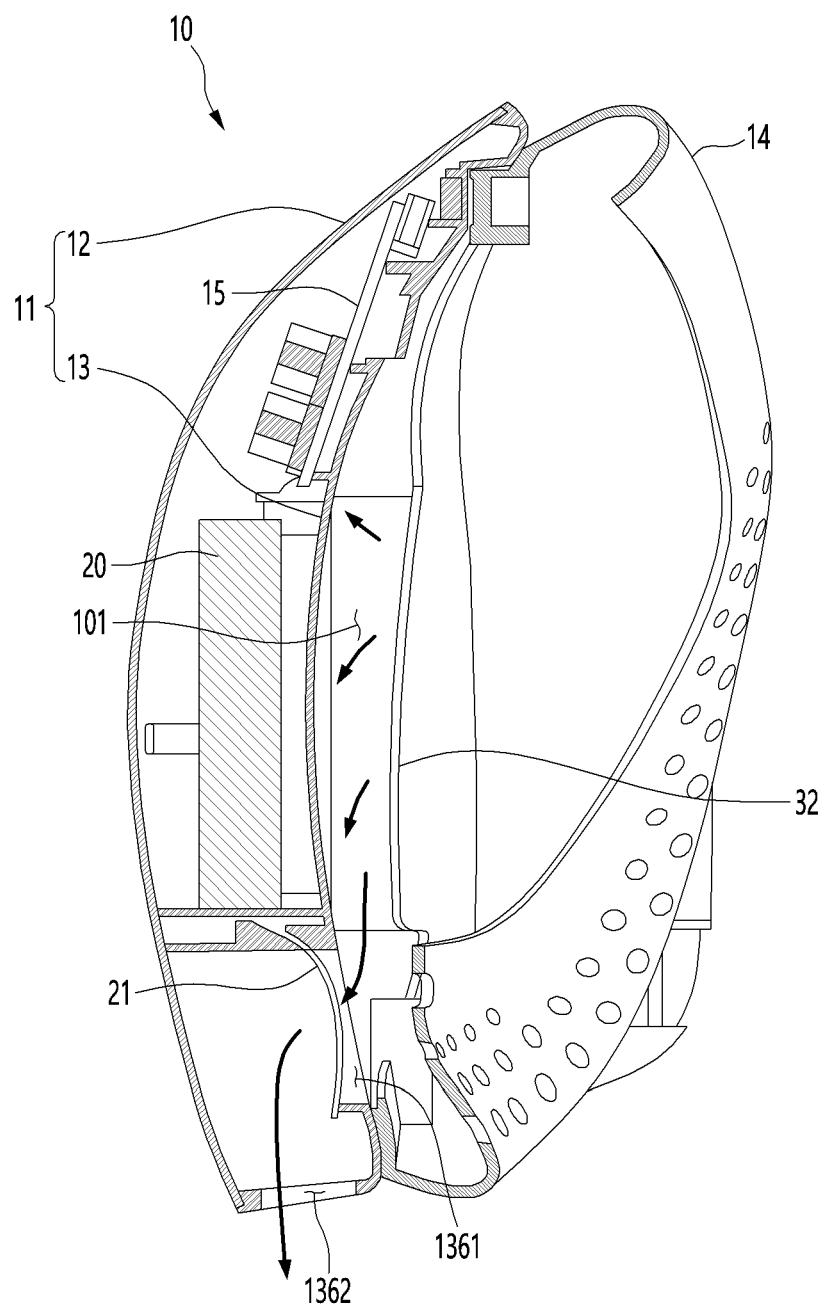
FIG. 9 is a longitudinal cross-sectional view of the mask apparatus.

FIG. 8 is a transverse cross-sectional view of the mask apparatus according to an embodiment, and FIG. 9 is a longitudinal cross-sectional view of the mask apparatus.

Referring to FIGS. 8 and 9, when the user operates the fan module 31 by pressing the power button, external air is introduced into the mask apparatus 10 through the suction grills 343 (or suction holes) disposed at the left and right sides of the rear surface of the mask apparatus 10.

The external air introduced through the suction grill 343 is purified while passing through the filter 33. Then, the air passing through the filter 33 is suctioned in an axial direction of the fan module 31 and then discharged in a radial direction.

As illustrated in FIG. 8, a front surface of the fan module 31 is seated on the seating surface 1331, and a rear surface of the fan module 31 is opened. In addition, the opened rear surface of the fan module 31 is shielded by the flow guide 32, and a communication hole serving as an suction hole of the fan module 31 is defined in the flow guide 32. The air passing through the filter 33 is introduced into the fan through the communication hole.

Also, an air duct 102 is defined between a side surface of the flow guide 32 and the air guide surface 1334. In addition, an inlet of the air duct 102 communicates with an outlet (or discharge hole) of the fan module 31, and the outlet of the air duct 102 communicates with the discharge hole 101.

In addition, the discharge hole 101 is defined in the breathing space defined by the rear surface of the face guard 14 and the rear body 13. Therefore, the external air suctioned by the fan module 31 is discharged to the breathing space, so that the user inhales.

In addition, the air guide surface 1334 is provided to be smoothly rounded from the outlet of the fan module 31 toward the discharge hole 101, so that the air discharged in the radial direction of the fan module 31 is not sharply changed in flow direction while flowing toward the discharge hole 101.

In detail, in the case of the centrifugal fan, the discharge of the air in the axial suction and radial discharge are due to a shape of a cone or truncated cone hub. That is, the air suctioned in the axial direction of the centrifugal fan is smoothly changed in direction to 90 degrees along the round surface of the hub.

Here, since the rounded direction of the hub constituting the fan module 31 and the rounded direction of the air guide surface 1334 are the same, the air suctioned into the fan module 31 smoothly flows in only one direction.

If the suction grill 343 is provided on the front body 12, the suction hole of the fan module 31 faces the front body 12, and as a result, the rounded direction of the hub constituting the fan module is opposite to the rounded direction of the air guide surface 1334. As a result, the air discharged from the fan module 31 collides with the beginning of the air guide surface 1334 corresponding to the suction hole of the air duct 102 to generate flow resistance and flow noise.

That is, the air suctioned in the axial direction of the fan module 31 substantially generates an S-shaped flow, resulting in a greater flow loss than the structure, in which the C-shaped or n-shaped flow is generated, according to an embodiment.

When the user exhales, the air discharged through the user's mouth and nose is collected in the breathing space. A minute portion of the air collected in the breathing space is introduced into the pressure sensor mounting portion 130 through the through-hole 1301.

In addition, most of the air collected in the breathing space descends and is discharged to the outside through the front exhaust port 1361 and the bottom exhaust port 1362. Here, as the exhaust valve 20 is bent forward by the pressure of air generated when the user exhales, the front exhaust port 1361 is opened. In addition, when the user inhales, the pressure inside the breathing space is lower than an atmospheric pressure, and the exhaust valve 20 returns to its original position to shield the front exhaust port 1361.

Figure 10:
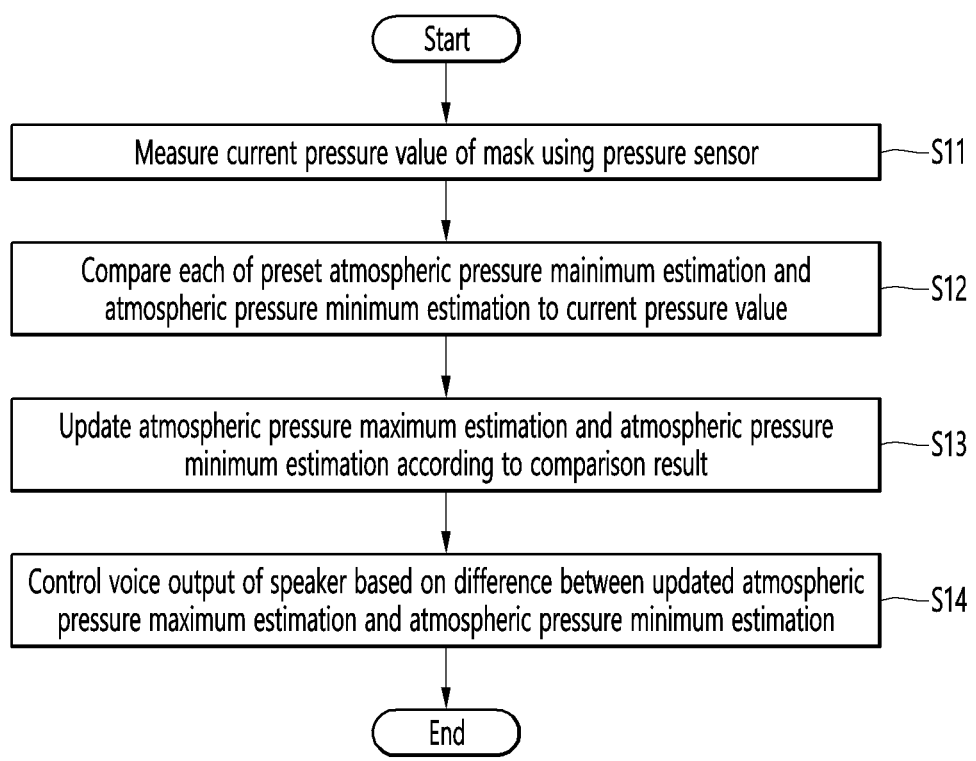
FIG. 10 is a schematic flowchart illustrating a method for controlling a mask apparatus according to an embodiment.

FIG. 10 is a schematic flowchart illustrating a method for controlling a mask apparatus according to an embodiment.

Referring to FIG. 10, a mask apparatus 10 measures a current pressure value of a mask using a pressure sensor 220.

The pressure sensor may be mounted on a pressure sensor mounting portion 130 disposed on a mask body 11. At least a portion of the pressure sensor may be disposed inside the pressure sensor mounting portion 130 to sense a pressure of a breathing space.

Here, the current pressure value of the mask may mean a pressure in a breathing space defined by the user's face and the face guard 14.

The pressure sensor may be an air pressure sensor that measures a pressure or air pressure in a sealed space using a flow rate or wind strength of introduced air. Alternatively, the pressure sensor may be a differential pressure sensor that measures a pressure change in a sealed space.

The mask apparatus 10 compares each of a preset atmospheric pressure estimation and an atmospheric pressure minimum estimation to a current pressure value and updates the atmospheric pressure maximum estimation and the atmospheric pressure minimum estimation according to the comparison result.

Here, the atmospheric pressure maximum estimation may be changed or updated in real time according to the maximum pressure value among the pressure values measured by the pressure sensor for a predetermined time.

The atmospheric pressure minimum estimation may be changed or updated in real time according to the minimum pressure value among pressure values measured by the pressure sensor for a predetermined time. Therefore, there is an advantage of high reliability because an error does not occur due to changes in the external environment (S12 and S13).

The mask apparatus 10 controls the voice output of the speaker based on a difference between the updated atmospheric pressure maximum estimation and the updated atmospheric pressure minimum estimation.

When the difference between the updated atmospheric pressure maximum estimation and the updated atmospheric pressure minimum estimation is less than the reference pressure value, the mask apparatus 10 may determine that the user takes off the mask and deactivate the speaker's voice output function or mute the sound.

In addition, when the difference between the updated atmospheric pressure maximum estimation and the updated atmospheric pressure minimum estimation is greater than the reference pressure value, the mask apparatus 10 may determine that the user wears the mask and activate the speaker's voice output function or release the mute state (S14).

Figure 11:
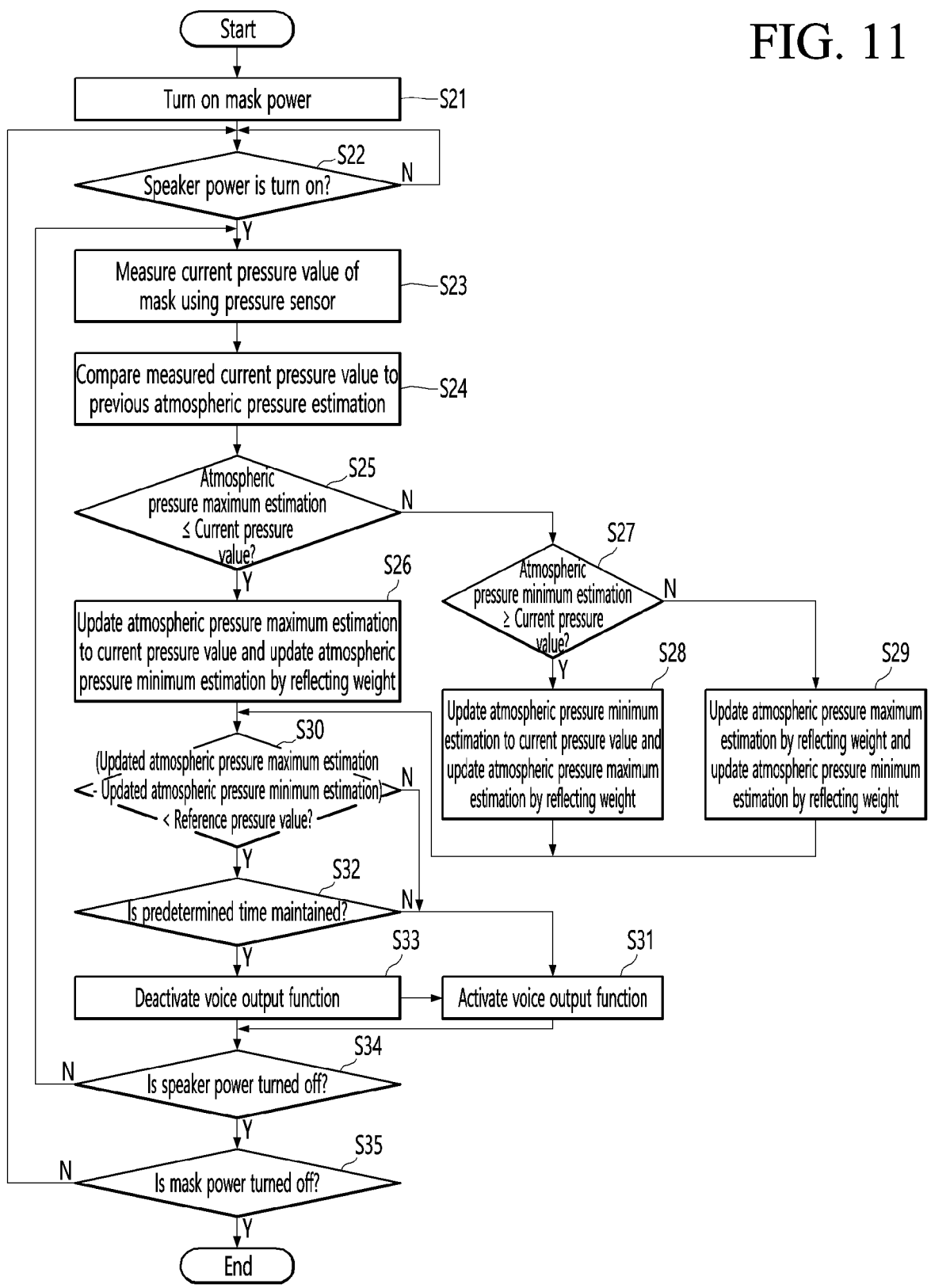
FIG. 11 is a detailed flowchart illustrating the method for controlling the mask apparatus according to an embodiment.

FIG. 11 is a detailed flowchart illustrating the method for controlling the mask apparatus according to an embodiment.

First, referring to FIG. 11, when the power of the mask apparatus 10 is turned on, it is determined whether the power of the speaker 19 is turned on.

Here, when the power of the speaker 19 is turned on, it may mean that the power of the speaker 19 and the power of the microphone are turned on together.

Also, even if the power of the speaker 19 is turned on, the output function (amplification function) of the speaker 19 is not unconditionally performed. For example, when the voice output function is deactivated even when the power of the speaker 19 is turned on, the output function of the speaker 19 may not be performed.

That is, the output function of the speaker 19 may be performed only when the voice output function is activated while the power of the speaker 19 is turned on.

The microphone is configured to receive an external sound or a user's voice. The microphone may be disposed in an inner space of the mask apparatus 10 to receive the user's voice clearly.

For example, the microphone may be disposed at one side of the breathing space of the mask apparatus 10. The microphone may be disposed inside the pressure sensor mounting portion 130 and may be disposed adjacent to the pressure sensor.

The power of the mask apparatus 10 may be turned on by pressing the power button (or a manipulation portion) provided at one side of the mask apparatus 10. In this case, when the power button is pressed for a predetermined time or more, the power of the mask apparatus 10 may be turned on.

When the power button is selected again in the state in which the mask apparatus 10 is powered on, the power of the speaker 19 may be turned on. Here, if the power button is selected again in the state in which the power of the speaker 19 is on, the power of the speaker 19 may be turned off.

In addition, when the power button is pressed for a predetermined time or more in the state in which the power of the mask apparatus 10 is turned on, the power of the mask apparatus 10 may be turned off.

In addition, the power of the mask apparatus 10 and the power of the speaker 19 may be manipulated by an external device communicatively connected thereto. For example, the mask apparatus 10 receives a control command from the external device (e.g., a mobile terminal, a computer, a wearable device, etc.), and the power of the mask apparatus 10 or the power of the speaker 19 may be turned on or off according to the control command.

According to this configuration, the user may operate the speaker 19 only when talking while wearing the mask apparatus 10. In addition, both the power of the mask apparatus 10 and the power of the speaker 19 may be manipulated by a simple operation of the power button (S21 and S22).

The mask apparatus 10 measures a current pressure value of the mask using the pressure sensor and compares the measured current pressure value to a previous atmospheric pressure estimation.

Here, the atmospheric pressure estimation may be an intermediate value defined between a maximum pressure value and a minimum pressure value among pressure values measured for a predetermined time by the pressure sensor.

The atmospheric pressure estimation may be updated in real time by following the current pressure value. The current atmospheric pressure estimation may be updated based on a preset atmospheric pressure estimation and a current pressure value. The updated atmospheric pressure estimation may be accumulated and stored in a memory of the mask apparatus 10.

In this embodiment, the atmospheric pressure estimation may be set as an intermediate value of the sum of an atmospheric pressure maximum estimation and an atmospheric pressure minimum estimation. The atmospheric pressure maximum estimation and the atmospheric pressure minimum estimation may be updated by following or converging the current pressure value. Thus, an error range of the updated atmospheric pressure estimation may be reduced, and reliability may be improved.

The mask apparatus 10 may compare each of the preset atmospheric pressure maximum estimation and the preset atmospheric pressure minimum estimation to the current pressure value and update the current atmospheric pressure estimation based on the difference (S23 and S24).

Hereinafter, a correlation between the current pressure value, the atmospheric pressure maximum estimation, the atmospheric pressure minimum estimation, and the atmospheric pressure estimation will be described with reference to the drawings.

Figure 12:
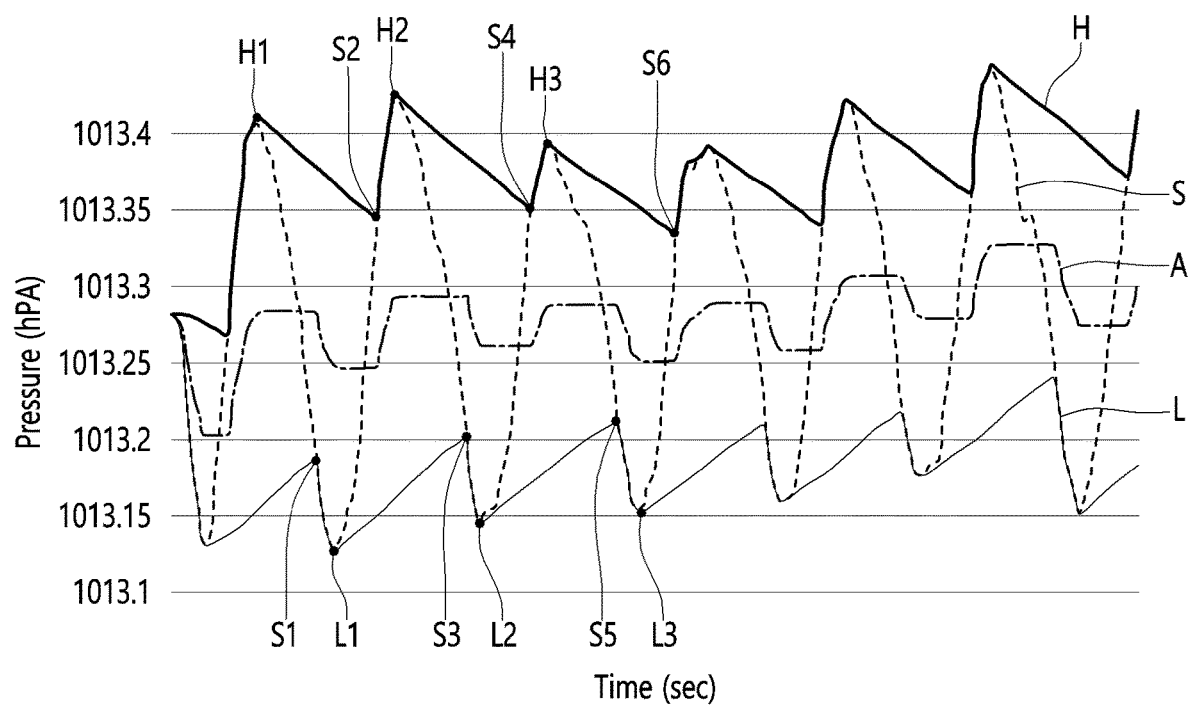
FIG. 12 is a graph showing a correlation between a current pressure value, an atmospheric pressure maximum estimation, an atmospheric pressure minimum estimation, and an atmospheric pressure estimation of a mask according to an embodiment.
Figure 13:
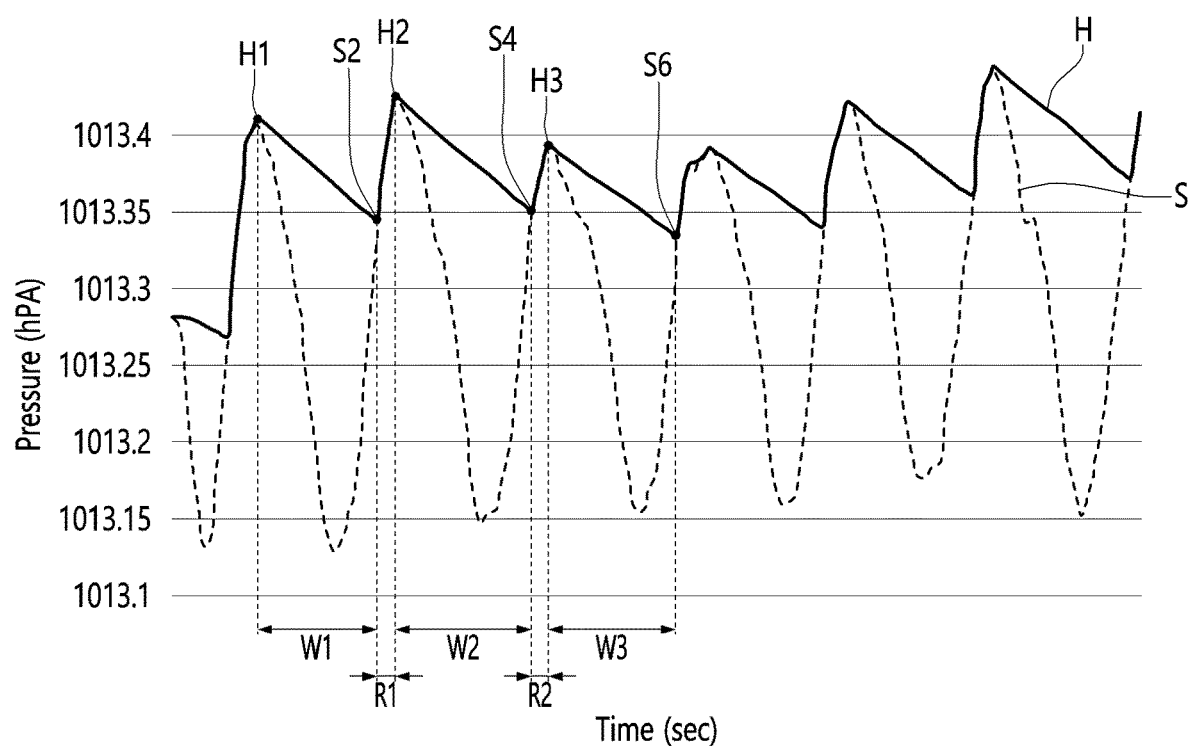
FIG. 13 is a graph in which the atmospheric pressure minimum estimation and the atmospheric pressure estimation are omitted from FIG. 12.
Figure 14:
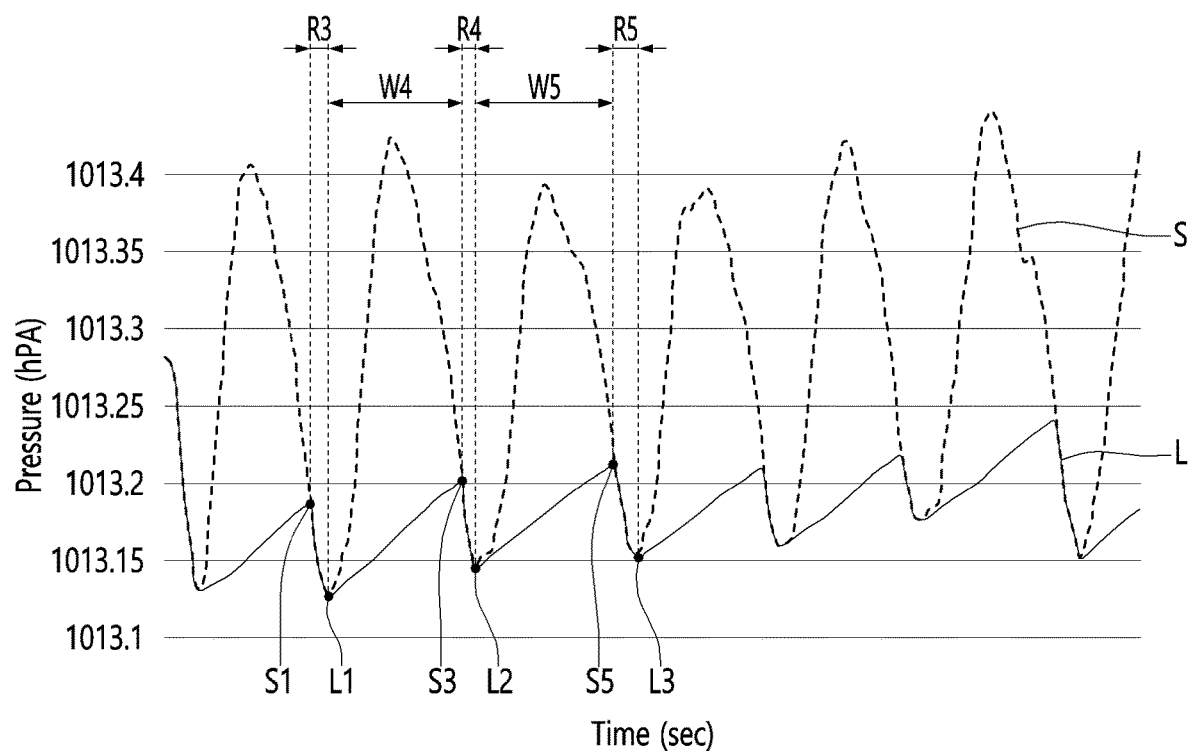
FIG. 14 is a graph in which the atmospheric pressure maximum estimation and the atmospheric pressure estimation are omitted from FIG. 12.
Figure 15:
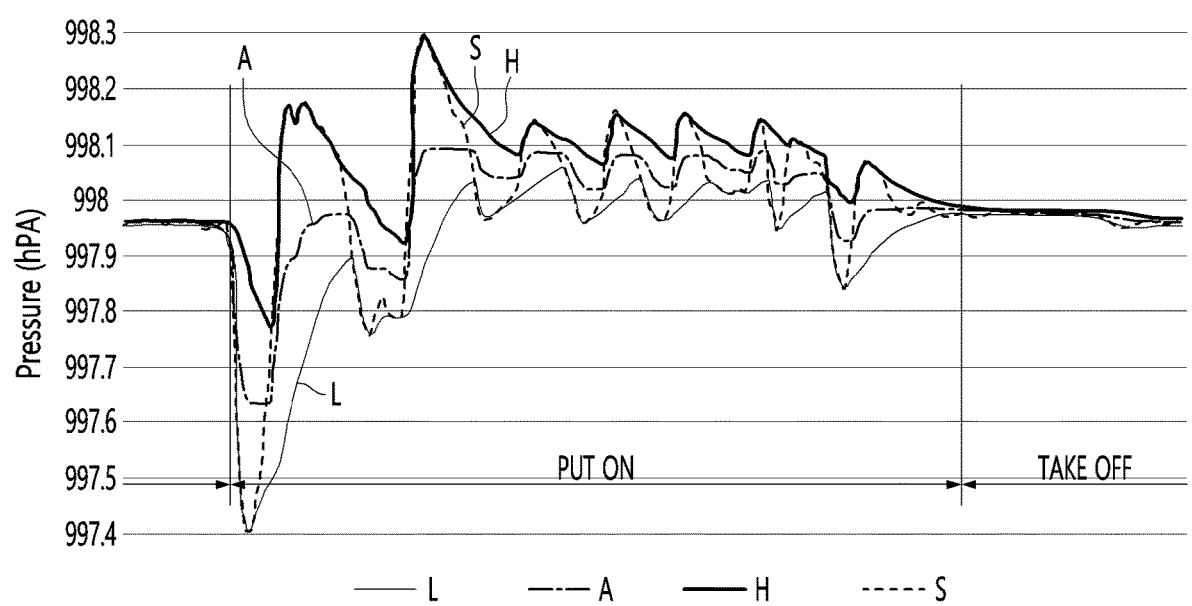
FIG. 15 is a graph showing a correlation between the current pressure value, the atmospheric pressure maximum estimation, the atmospheric pressure minimum estimation, and the atmospheric pressure estimation of the mask in a state in which a user wears the mask and takes off the mask.

FIG. 12 is a graph showing a correlation between the current pressure value, the atmospheric pressure maximum estimation, the atmospheric pressure minimum estimation, and the atmospheric pressure estimation of a mask according to an embodiment, FIG. 13 is a graph in which the atmospheric pressure minimum estimation and the atmospheric pressure estimation are omitted from FIG. 12, FIG. 14 is a graph in which the atmospheric pressure maximum estimation and the atmospheric pressure estimation are omitted from FIG. 12, and FIG. 15 is a graph showing a correlation between the current pressure value, the atmospheric pressure maximum estimation, the atmospheric pressure minimum estimation, and the atmospheric pressure estimation of the mask in a state in which the user wears the mask and takes off the mask.

Referring to FIGS. 12 to 15, a horizontal axis of the graph indicates the passage of time, and a vertical axis of the graph indicates an amount of change in pressure. In FIGS. 12 to 15, a dotted line S indicates a current pressure value, a thick solid line H indicates an atmospheric pressure maximum estimation, a thin solid line L indicates an atmospheric pressure minimum estimation, and a dashed-dotted line A indicates an atmospheric pressure estimation.

Referring to FIGS. 12 to 15, a graph of the sensor pressure value S measured by the pressure sensor draws a sine wave according to a person's breathing cycle, i.e., inhalation and exhalation.

For example, the sensor pressure value S decreases in an inhaling state in which the user inhales, and the sensor pressure value S increases in an exhalation state in which the user exhales.

The sensor pressure value S may have maximum pressure values H1, H2, and H3 and minimum pressure values L1, L2, and L3 according to each breathing cycle.

In an embodiment, an atmospheric pressure maximum estimation and an atmospheric pressure minimum estimation may be updated by following the maximum pressure values H1, H2, and H3 and the minimum pressure values L1, L2, and L3 of the sensor pressure value S, and the atmospheric pressure estimation may be updated based on the updated atmospheric pressure maximum estimation and the atmospheric pressure minimum estimation.

Specifically, the mask apparatus 10 determines whether the preset atmospheric pressure maximum estimation is equal to or less than the current pressure value. Here, if the preset atmospheric pressure maximum estimation is equal to or less than the current pressure value, the preset atmospheric pressure maximum estimation is updated to the current pressure value, and the preset atmospheric pressure minimum estimation is updated by reflecting a weight.

When it is determined that the preset atmospheric pressure maximum estimation is equal to or less than the current pressure value, the preset atmospheric pressure maximum estimation may follow the current pressure value. That is, when it is determined that the preset atmospheric pressure maximum estimation is equal to or less than the current pressure value, the preset atmospheric pressure maximum estimation may increase along the current pressure value and then may be the same as the current pressure value.

Here, when the preset atmospheric pressure maximum estimation is equal to or less than the current pressure value, a period (time point) in which the atmospheric pressure maximum estimation is updated to the current pressure value may be defined as first update periods R1 and R2 (S25 and S26).

When the preset atmospheric pressure maximum estimation exceeds the current pressure value, the mask apparatus 10 determines whether the preset atmospheric pressure minimum estimation is equal to or greater than the current pressure value. Here, if the preset atmospheric pressure minimum estimation is equal to or greater than the current pressure value, the preset atmospheric pressure minimum estimation is updated to the current pressure value, and the preset atmospheric pressure minimum estimation is updated by reflecting a weight.

When it is determined that the preset atmospheric pressure minimum estimation is equal to or greater than the current pressure value, the preset atmospheric pressure minimum estimation may follow the current pressure value. That is, when it is determined that the preset atmospheric pressure minimum estimation is equal to or greater than the current pressure value, the preset atmospheric pressure minimum estimation may decrease along the current pressure value and then may be the same as the current pressure value.

Here, when the preset atmospheric pressure minimum estimation is equal to or greater than the current pressure value, a period (time point) in which the atmospheric pressure minimum estimation is updated to the current pressure value may be defined as second update periods R3, R4, and R5.

Here, the first update periods R1 and R2 and the second update periods R3, R4, and R5 do not overlap each other (S27 and S28).

When the preset atmospheric pressure maximum estimation exceeds the current pressure value, and the preset atmospheric pressure maximum estimation is less than the current pressure value, each of the preset atmospheric pressure maximum estimation and the preset atmospheric pressure maximum estimation may be updated by reflecting the weight.

In detail, when the atmospheric pressure maximum estimation is not updated by following the current pressure value, the mask apparatus 10 may update the atmospheric pressure maximum estimation to converge to the preset atmospheric pressure estimation by reflecting the weight.

According to this embodiment, Equation for updating the atmospheric pressure maximum estimation by reflecting the weight is as follows.

$$(APME)_n = (APME)_{n-1} - ((APME)_{n-1} - (APE)_{n-1}) \times \text{Weight} \quad [\text{Equation 1}]$$

In Equation 1, "APME" may indicate an atmospheric pressure maximum estimation, "APE" may indicate an atmospheric pressure estimation, and "Weight" may indicate a preset weight.

The "Weight" may be a preset constant and may be a reciprocal number of a value obtained by multiplying a person's "maximum breathing time (sec)" and "sensor update period (Hz)".

For example, the maximum breathing time may be about 4 seconds, and the sensor update cycle may be about 75 Hz. However, an embodiment of the present disclosure is not limited thereto, and the maximum breathing time and the sensor update period may be set in various manners.

In addition, according to this embodiment, Equation for updating the atmospheric pressure minimum estimation by reflecting the weight is as follows.

$$(APNE)_n = (APNE)_{n-1} + ((APE)_{n-1} - (APNE)_{n-1}) \times \text{Weight} \quad [\text{Equation 2}]$$

In Equation 2, "APNE" may indicate an atmospheric pressure minimum estimation, "APE" may indicate an atmospheric pressure estimation, and "Weight" may indicate a preset weight.

The "Weight" may be a preset constant and may be a reciprocal number of a value obtained by multiplying a person's "maximum breathing time (sec)" and "sensor update period (Hz)".

For example, the maximum breathing time may be about 4 seconds, and the sensor update cycle may be about 75 Hz. However, an embodiment of the present disclosure is not limited thereto, and the maximum breathing time and the sensor update period may be set in various manners.

As described above, an n-th atmospheric pressure maximum estimation may be updated based on an (n−1)-th atmospheric pressure maximum estimation and an (n−1)-th atmospheric pressure estimation, and the n-th atmospheric pressure minimum estimation may be updated based on the (n−1)-th atmospheric pressure minimum estimation and the (n−1)-th atmospheric pressure estimation.

Therefore, to update the atmospheric pressure estimation, since only the current pressure value and the previous atmospheric pressure estimation data are required, there is an advantage in that a memory capacity for data accumulation is minimized, and a data processing time is reduced.

Here, a period (time point) in which the atmospheric pressure maximum estimation is updated to converge to the atmospheric pressure estimation may be defined as first convergence periods W1, W2, and W3, and a period (time point) in which the atmospheric pressure minimum estimation is updated to converge to the atmospheric pressure estimation may be defined as second convergence periods W4 and W5.

In summary, when each of the atmospheric pressure maximum estimation and the atmospheric pressure minimum estimation meets a predetermined condition, the mask apparatus 10 may update the atmospheric pressure maximum estimation and the atmospheric pressure minimum estimation by following the current pressure value, and when each of the atmospheric pressure maximum estimation and the atmospheric pressure minimum estimation does not meet the predetermined condition, weights (application of Equations 1 and 2) may be reflected in the atmospheric pressure maximum estimation and the atmospheric pressure minimum estimation so as to be updated to converge to the atmospheric pressure estimation (S27 and S29).

As described in the operations S24 to S29, when the atmospheric pressure maximum estimation and the atmospheric pressure minimum estimation are updated, the mask apparatus 10 determines whether a difference value between the updated atmospheric pressure maximum estimation and the updated atmospheric pressure maximum estimation is less than the reference pressure value.

Here, the reason for determining whether the difference between the updated atmospheric pressure maximum estimation and the updated atmospheric pressure minimum estimation is less than the reference pressure value is for checking whether the user wears the mask.

Specifically, as illustrated in FIG. 15, when a person breathes while wearing the mask apparatus 10, a difference between an atmospheric pressure maximum estimation H and an atmospheric pressure minimum estimation L may be about 5 Pascals (Pa) or more. On average, when the person breathes while wearing the mask apparatus 10, the difference between the atmospheric pressure maximum estimation H and the atmospheric pressure minimum estimation L may be about 10 Pascals to about 20 Pascals.

Conversely, when the person takes off the mask apparatus 10, the difference between the atmospheric pressure maximum estimation H and the atmospheric pressure minimum estimation L may be less than about 5 Pascals. On average, in the state in which the person does not wear the mask apparatus 10, the difference between the atmospheric pressure maximum estimation H and the atmospheric pressure minimum estimation L may be about 1 pascal to about 3 Pascals.

Therefore, in this embodiment, when the difference between the atmospheric pressure maximum value H and the atmospheric pressure minimum estimation L is less than about 5 Pascals, it is determined that the user takes off the mask, and when the difference is about 5 Pascals or more, it is determined that the user wears the mask. However, the reference pressure value may be about 5 Pascals, but is not limited thereto (S30).

As a result of the determination, when the difference between the updated atmospheric pressure maximum estimation and the updated atmospheric pressure minimum estimation is equal to or greater than the reference pressure value, the mask apparatus 10 activates the voice output function.

Specifically, when the difference value between the updated atmospheric pressure maximum estimation and the updated atmospheric pressure minimum estimation is greater than the reference pressure value, it means that the user is in a state in which utterance is possible while wearing the mask. Thus, the mask apparatus 10 may activate the voice output of the speaker 19.

In this case, the activation of the voice output of the speaker 19 may include a process of amplifying an input signal level of the voice signal input from the microphone or a process of releasing the mute state of the microphone. Thus, when the user speaks while wearing the mask, the voice may be amplified and output to the outside (S31).

On the other hand, when a time at which the difference between the updated atmospheric pressure maximum estimation and the updated atmospheric pressure minimum estimation is less than the reference pressure value is maintained for a predetermined time or more, the mask apparatus 10 deactivates the voice output function.

Here, the reason for determining that the time at which the difference value is less than the reference pressure value is maintained for a predetermined time or more is for accurately determining whether the mask is worn. For example, the mask apparatus 10 may determine whether the time at which the difference value is less than the reference pressure value is maintained for about 1 second or more.

Specifically, when the difference between the updated atmospheric pressure maximum estimation and the updated atmospheric pressure minimum estimation is less than the reference pressure value, it means that the user does not wear the mask. Thus, the mask apparatus 10 may deactivate the voice output of the speaker 19.

Here, the deactivation of the voice output of the speaker 19 may include a process of ignoring the input signal of the voice signal input from the microphone or a process of muting a sound output from the microphone. Thus, fan noise and noise caused by a howling phenomenon generated when the user takes off the mask apparatus 10 may be prevented from being output to the outside through the speaker 19 (S32 and S33).

Thereafter, the mask apparatus 10 determines whether the power of the speaker 19 is turned off, and if the power of the speaker 19 is not turned off, the process proceeds to operation S23 so as to measure the current pressure value of the mask again (S34).

If the power of the speaker 19 is turned off, the mask apparatus 10 determines whether the mask power is off, and if the mask power is off, an algorithm is ended, and if the mask power is not off, the process proceeds to operation S22 to determine again whether the power of the speaker 19 is turned on (S35).

Figure 16:
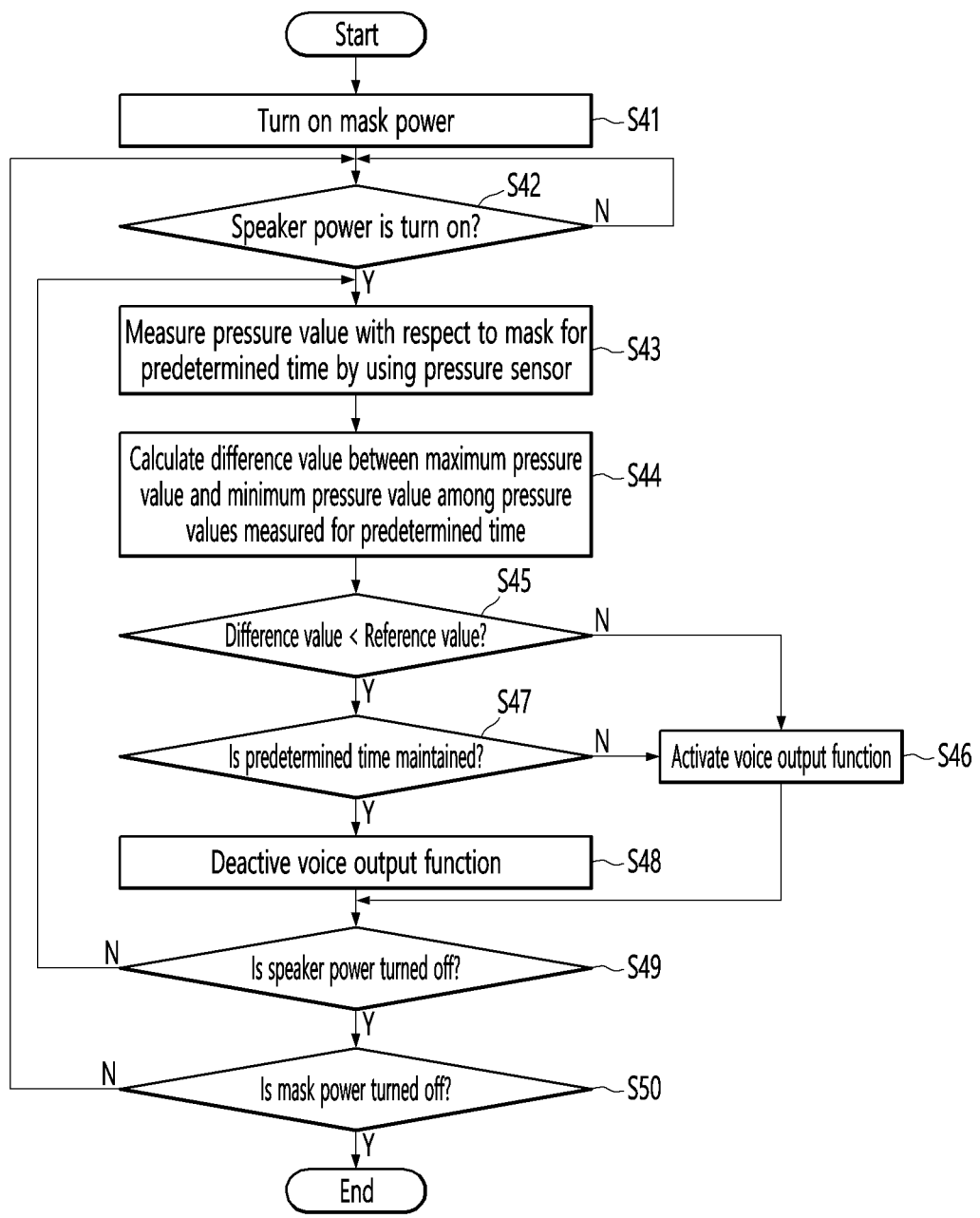
FIG. 16 is a flowchart illustrating a method for controlling a mask apparatus according to another embodiment.
Figure 17:
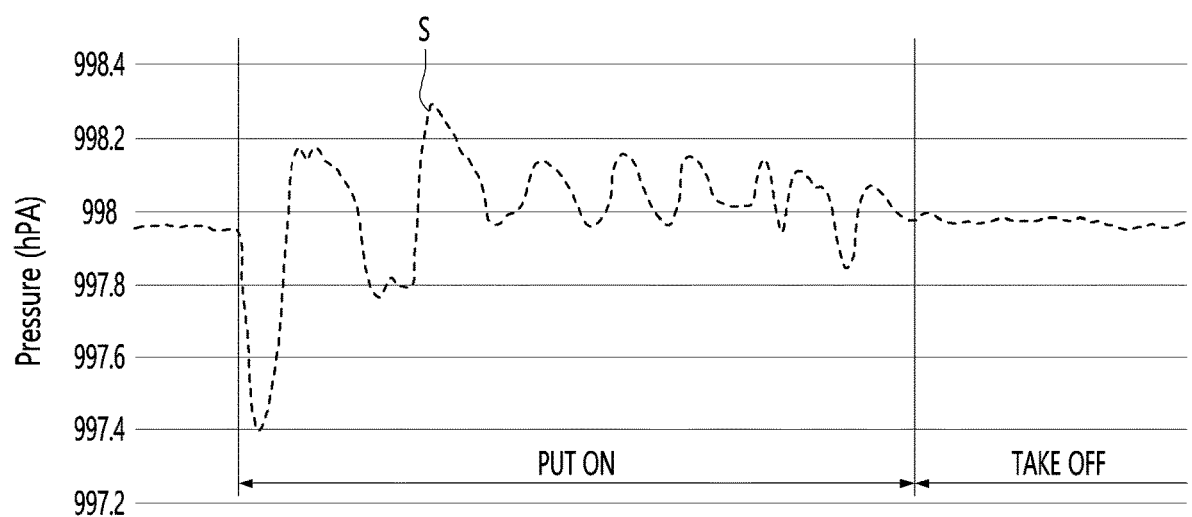
FIG. 17 is a graph showing a current pressure value of a mask in a state in which the user wears and takes off the mask.

FIG. 16 is a flowchart illustrating a method for controlling a mask apparatus according to another embodiment, and FIG. 17 is a graph showing a current pressure value of a mask in a state in which the user wears and takes off the mask.

First, referring to FIG. 16, when power of a mask apparatus 10 is turned on, it is determined whether power of a speaker 19 is turned on (S41 and S42).

When the power of the speaker 19 is turned on, the mask apparatus 10 measures a current pressure value of the mask using a pressure sensor.

For example, the mask apparatus 10 may acquire a pressure value of the mask for about 2 seconds through the pressure sensor. Alternatively, the mask apparatus 10 may acquire the pressure value of the mask for a time corresponding to a user's one-time breathing cycle through the pressure sensor.

Here, the reason why the mask apparatus 10 measures the pressure value for a certain time is for accurately determining whether the user wears the mask. The predetermined time may be about 2 seconds, but is not limited thereto (S43).

The mask apparatus 10 calculates a difference value between a maximum pressure value and a minimum pressure value among pressure values measured for a predetermined time and determines whether the calculated difference value is less than a reference pressure value.

Here, the reason for determining whether the difference between the maximum pressure value and the minimum pressure value is less than the reference pressure value is for determining whether the user wears the mask.

Specifically, as illustrated in FIG. 17, when a person breathes while wearing the mask apparatus 10, the difference between the maximum pressure value and the minimum pressure value measured by the pressure sensor is about 5 Pascals or more. On average, when a person breathes while wearing the mask apparatus 10, the difference between the measured maximum pressure value and the measured minimum pressure value may be about 10 Pascals to about 20 Pascals.

Conversely, when the person takes off the mask apparatus 10, the difference between the measured maximum pressure value and the minimum pressure value may be less than about 5 Pascals. On average, when the person does not wear the mask apparatus 10, the difference between the measured maximum pressure value and the minimum pressure value may be about 1 Pascal to about 3 Pascals.

Therefore, in the present embodiment, when the difference between the measured maximum pressure value and the minimum pressure value is less than about 5 Pascals, it is determined that the user takes off the mask, and when the difference is about 5 Pascals or more, it is determined that the user wears the mask. However, the reference pressure value may be about 5 Pascals, but is not limited thereto (S44 and S30).

As a result of the determination, when the difference between the measured maximum pressure value and the measured minimum pressure value is equal to or greater than the reference pressure value, the mask apparatus 10 activates a voice output function.

Specifically, when the difference between the measured maximum pressure value and the minimum pressure value is greater than the reference pressure value, it means that the user is in a state in which utterance is possible while wearing the mask. Thus, the mask apparatus 10 may activate the voice output of the speaker 19.

In this case, the activation of the voice output of the speaker 19 may include a process of amplifying an input signal level of the voice signal input from the microphone or a process of releasing the mute state of the microphone. Thus, when the user speaks while wearing the mask, the voice may be amplified and output to the outside (S46).

On the other hand, when the time at which the difference between the measured maximum pressure value and the minimum pressure value is detected to be less than the reference pressure value is maintained for a predetermined time or more, the mask apparatus 10 deactivates the voice output function.

Here, the reason for determining that the time at which the difference value is less than the reference pressure value is maintained for a predetermined time or more is for accurately determining whether the mask is worn. For example, the mask apparatus 10 may determine whether the time at which the difference value is less than the reference pressure value is maintained for about 1 second or more.

Specifically, when the difference between the measured maximum pressure value and the minimum pressure value is less than the reference pressure value, it means that the user does not wear the mask. Thus, the mask apparatus 10 may deactivate the voice output of the speaker 19.

Here, the deactivation of the voice output of the speaker 19 may include a process of ignoring the input signal of the voice signal input from the microphone or a process of muting a sound output from the microphone. Thus, fan noise and noise caused by a howling phenomenon generated when the user takes off the mask apparatus 10 may be prevented from being output to the outside through the speaker 19 (S47 and S48).

Thereafter, the mask apparatus 10 determines whether the power of the speaker 19 is turned off, and if the power of the speaker 19 is not turned off, the process proceeds to operation S23 so as to measure the current pressure value of the mask again (S49).

If the power of the speaker 19 is turned off, the mask apparatus 10 determines whether the mask power is off, and if the mask power is off, an algorithm is ended, and if the mask power is not off, the process proceeds to operation S22 to determine again whether the power of the speaker 19 is turned on (S50).

According to the constituents as described above, following effects may be expected.

First, when the mask is taken off, the driving of the fan may be automatically stopped, and thus, the fan noise may be prevented, and the power consumption by driving the fan may be prevented.

Second, when the mask is taken off, since the speaker is automatically stopped, there may be the advantage in that the fan noise and the noise due to the howling is prevented from occurring.

Third, since the operations of the fan and the speaker is automatically controlled without the separate function button operation, the mask touch may be reduced to improve the convenience and the sanitary condition of the mask.

Fourth, since it is determined whether the mask is worn by using the atmospheric pressure estimation based on the internal pressure of the mask, there may be the advantage in that whether the mask is worn is accurately determined regardless of the change in external environment.

Fifth, since it is determined whether the mask is worn using only the pressure value inside the mask or the previous atmospheric pressure estimation, the memory capacity for data accumulation may be minimized, and the data processing time may be reduced. Therefore, there may be the advantage that it is possible to quickly determine the state of wearing the mask and reducing the cost.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A method for controlling a mask apparatus, the method comprising:
    measuring a current pressure value with respect to a mask by using a pressure sensor;
    comparing each of a preset atmospheric pressure maximum estimation and a preset atmospheric pressure minimum estimation to the current pressure value;
    updating the atmospheric pressure maximum estimation and the atmospheric pressure minimum estimation according to the comparison result; and
    controlling a voice output of a speaker based on a difference between the updated atmospheric pressure maximum estimation and the updated atmospheric pressure minimum estimation,
    wherein the atmospheric pressure maximum estimation is changed or updated in real time according to a maximum pressure value among pressure values measured by the pressure sensor for a predetermined time, and
    wherein the atmospheric pressure minimum estimation is changed or updated in real time according to a minimum pressure value among the pressure values measured by the pressure sensor for the predetermined time.

2. The method according to claim 1, wherein the controlling of the voice output of the speaker based on the difference between the updated atmospheric pressure maximum estimation and the updated atmospheric pressure minimum estimation comprises:
    calculating a difference value between the updated atmospheric pressure maximum estimation and the updated atmospheric pressure minimum estimation;
    comparing the difference value to a reference pressure value; and
    controlling the voice output of the speaker according to the comparison result of the difference value and the reference pressure value.

3. The method according to claim 2, wherein, when the difference value is less than the reference pressure value, a voice output function of the speaker is deactivated, or a voice is muted.

4. The method according to claim 2, wherein, when the difference value is greater than the reference pressure value, a voice output function of the speaker is activated, or a mute state is released.

5. The method according to claim 1, further comprising controlling an operation of a fan module based on a difference between the updated atmospheric pressure maximum estimation and the updated atmospheric pressure minimum estimation.

6. The method according to claim 1,
    wherein the updating of the atmospheric pressure maximum estimation and the atmospheric pressure minimum estimation according to the comparison result comprises, when the preset atmospheric pressure maximum estimation is less than the current pressure value:
        updating the preset atmospheric pressure maximum estimation to the current pressure value; and
        updating the preset atmospheric pressure minimum estimation by reflecting a weight, and
    wherein the weight is a reciprocal number of a value obtained by multiplying a person's "maximum breathing time (sec)" and "sensor update period (Hz)".

7. The method according to claim 6, wherein:
    when the preset atmospheric pressure maximum estimation exceeds the current pressure value, the preset atmospheric pressure minimum estimation and the current pressure value are compared to each other, and
    when the preset atmospheric pressure minimum estimation is equal to or greater than the current pressure value, the preset atmospheric pressure minimum estimation is updated to the current pressure value to update the preset atmospheric pressure maximum estimation by reflecting the weight.

8. The method according to claim 7, wherein, when the preset atmospheric pressure maximum estimation exceeds the current pressure value, and the preset atmospheric pressure maximum estimation is less than the current pressure value, each of the preset atmospheric pressure maximum estimation and the preset atmospheric pressure maximum estimation is updated by reflecting the weight.

9. A mask apparatus comprising:
    a mask body in which a microphone and a speaker are installed;

a face guard coupled to the mask body so as to be in close contact with a user's face and having a breathing space therein;

a pressure sensor installed in the mask body to measure a pressure of the breathing space; and a controller configured to:
  compare a preset atmospheric pressure maximum estimation and a preset atmospheric pressure minimum estimation to a current pressure value measured by the pressure sensor;
  update the atmospheric pressure maximum estimation and the atmospheric pressure minimum estimation according to the comparison result; and
  control a voice output of the speaker based on a difference between the updated atmospheric pressure maximum estimation and the updated atmospheric pressure minimum estimation, wherein the atmospheric pressure maximum estimation is changed or updated in real time according to a maximum pressure value among pressure values measured by the pressure sensor for a predetermined time, and wherein the atmospheric pressure minimum estimation is changed or updated in real time according to a minimum pressure value among the pressure values measured by the pressure sensor for the predetermined time.

10. The mask apparatus according to claim 9, wherein the controller is configured to:
  calculate a difference value between the updated atmospheric pressure maximum estimation and the updated atmospheric pressure minimum estimation; and
  control the voice output of the speaker according to the comparison result of the difference value and a reference pressure value.

11. The mask apparatus according to claim 10, wherein, when the difference value is less than the reference pressure value, the controller is configured to deactivate a voice output function of the speaker or mute a voice.

12. The mask apparatus according to claim 10, wherein, when the difference value is greater than the reference pressure value, the controller is configured to activate a voice output function of the speaker or release a mute state.

13. The mask apparatus according to claim 9, further comprising a fan module installed in the mask body,
  wherein the controller is configured to control an operation of the fan module based on a difference between the updated atmospheric pressure maximum estimation and the updated atmospheric pressure minimum estimation.

14. The mask apparatus according to claim 9,
  wherein, when the preset atmospheric pressure maximum estimation is less than the current pressure value, the controller is configured to:
    update the preset atmospheric pressure maximum estimation to the current pressure value; and
    update the preset atmospheric pressure minimum estimation by reflecting a weight, and
  wherein the weight is a reciprocal number of a value obtained by multiplying a person's "maximum breathing time (sec)" and "sensor update period (Hz)".

15. The mask apparatus according to claim 14, wherein:
  when the preset atmospheric pressure maximum estimation exceeds the current pressure value, the controller is configured to compare the preset atmospheric pressure minimum estimation to the current pressure value, and
  when the preset atmospheric pressure minimum estimation is equal to or greater than the current pressure value, the controller is configured to: update the preset atmospheric pressure minimum estimation to the current pressure value; and update the preset atmospheric pressure maximum estimation by reflecting the weight.

16. The mask apparatus according to claim 15, wherein, when the preset atmospheric pressure maximum estimation exceeds the current pressure value, and the preset atmospheric pressure maximum estimation is less than the current pressure value, the controller is configured to update each of the preset atmospheric pressure maximum estimation and the preset atmospheric pressure maximum estimation by reflecting the weight.

* * * * *